United States Patent [19]

Breipohl et al.

[11] Patent Number: 4,861,755

[45] Date of Patent: Aug. 29, 1989

[54] PEPTIDES WITH VASORELAXANT, NATRIURETIC AND DIURETIC EFFECTS A PROCESS FOR THEIR PREPARATION, AGENTS CONTAINING THEM, AND THEIR USE

[75] Inventors: Gerhard Breipohl, Frankfurt am Main; Jochen Knolle, Kriftel; Wolfgang König, Hofheim am Taunus; Bernward Schölkens, Kelkheim, all of Fed. Rep. of Germany

[73] Assignee: Hoechst Aktiengesellschaft, Frankfurt am Main, Fed. Rep. of Germany

[21] Appl. No.: 3,237

[22] Filed: Jan. 14, 1987

[30] Foreign Application Priority Data

Jan. 16, 1986 [DE] Fed. Rep. of Germany ....... 3601049
May 2, 1986 [DE] Fed. Rep. of Germany ....... 3614833

[51] Int. Cl.⁴ ..................... A61K 37/02; C07K 7/10; C07K 7/08
[52] U.S. Cl. ........................................ 514/11; 514/12; 514/13; 530/324; 530/325; 530/326
[58] Field of Search ............... 530/326, 325, 324, 317, 530/321; 514/12, 13, 11, 9

[56] References Cited

U.S. PATENT DOCUMENTS 4,496,544 1/1985 Needleman ........................... 514/13

FOREIGN PATENT DOCUMENTS 140731 5/1985 European Pat. Off. .
142487 5/1985 European Pat. Off. .
152333 8/1985 European Pat. Off. .

Primary Examiner—Delbert R. Phillips
Assistant Examiner—Christina Chan
Attorney, Agent, or Firm—Finnegan, Henderson, Farabow, Garret, & Dunner

[57] ABSTRACT

The invention relates to new peptides of the formula

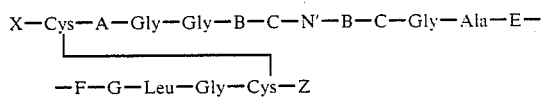

in which X, A, B, C, N', E, F, G and Z have the meanings indicated in the description, to a process for their preparation, to agents containing them, and to their use.

13 Claims, No Drawings

PEPTIDES WITH VASORELAXANT, NATRIURETIC AND DIURETIC EFFECTS A PROCESS FOR THEIR PREPARATION, AGENTS CONTAINING THEM, AND THEIR USE

European Patents A2-140,731, A2-142,487 and A2-152,333 disclose peptides whose sequence represents a part sequence of the natural atrial natriuretic factor (ANF) of humans or rats.

The invention relates to new peptides of the formula I

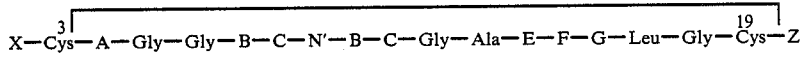

in which X denotes $(C_1-C_{12})$-alkanecarbonyl or $(C_3-C_8)$-cycloalkanecarbonyl, each of which is optionally branched in the α-position and is optionally monosubstituted in the ω-position by amino or guanidino, or represents Ser, Thr, Ser(Y), Thr(Y), Q or Leu, each in their L-or D-configuration, or Ser-Ser, Thr-Thr, Ser-Thr, Q-ser, Q-Thr, Thr-Q, Ser-Q, Ser(Y)-Ser or Ser-Ser(Y), wherein each amino acid is in its L- or D-configuration and the N-terminal amino group of the amino acid or of the dipeptide residue being free (N-terminal residue=H) or acylated by $(C_1-C_5)$-alkoxy carbonyl, $(C_6-C_{12})$-aryloxycarbonyl, $(C_7-C_{13})$-aralkyloxycarbonyl, $(C_1-C_6)$-alkanoyl, $(C_7-C_{13})$-aroyl, arginyl, lysyl, ε-aminocaproyl, arginylarginyl, arginyl-lysyl, lysyl-arginyl or lysyl-lysyl; A denotes Phe, Trp or an L-2-thienylalanine residue; B denotes Arg, Lys, Orn or an L-homoarginine residue; C denotes Ile, Met, Phe, Trp, Leu, Ser, Thr, Val, His, Pro, Asn, Ser(Bu$^t$) or L-2-thienylalanine residue; N' denotes Asp, Glu, Gln, Asn, Phe, Leu, Ile, Trp, Pro, Tyr, Ala, Asp(OBu$^t$), Asp(OBzl), Glu(OBu$^t$), Glu(OBzl), a 2-thienylalanine residue, Aad, Tyr(Bu$^t$) or Tyr(Me),
wherein each of the amino acids is in their L- or D-configuration;
E denotes Gln, Thr or Pro;
F denotes Ser, Thr, Pro, Ala, Ser(Bu$^t$) or Thr(Bu$^t$), each in their L-or D-configuration;
G denotes Gly, Ala or D-Ala;
Q denotes a radical of the formula IV

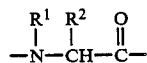

in which
$R^1$ and $R^2$, together with the atoms carrying these radicals, form a heterocyclic mono-, bi- or tri-cyclic ring system having 3 to 15 carbon atoms;
Y denotes tert.-butyl or an optionally protected or partially protected glycosyl radical; and Z represents a residue of the formula II

—H—I—J—K—L—M (II)

in which
H denotes Asn, Ser, Q or Thr, each in their L- or D-form;
I denotes Ser, Thr, Ala, Ser(Bu$^t$), Thr(Bu$^t$), or Pro, each in their L- or D-form;
J denotes Phe, Trp, D-Phe, D-Trp or a 2-thienylalanine residue;
K denotes Arg, Lys, Orn or a bond;
L denotes Tyr, Tyr(Bu$^t$) or a bond:
M denotes Arg-OH, Arg-NH$_2$, OH, OR, NH$_2$, NHR', Gly-Lys-Arg-OH, Gly-Lys-Arg-NH$_2$ or L-argininol;
Q is as defined above;
R denotes unbranched $(C_1-C_6)$-alkyl, and
R' denotes —[CH$_2$]$_n$—NH$_2$ or —]CH$_2$[$_n$—NH—C(NH)NH$_2$, n being an integer and representing 3–8; and to their physiologically tolerated salts, an exception being made of the peptides, corresponding to the sequence of natural ANF, of the formula III

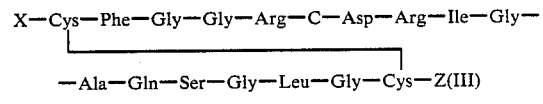

in which
X denotes Ser, Ser-Ser, Arg-Ser-Ser or Arg-Arg-Ser-Ser,
C denotes Ile or met,
Z denotes Asn-Ser-Phe-K-L-M,
K denotes Arg or a bond,
L denotes Tyr or a bond and
M denotes OH or NH$_2$, and their salts.

A particularly suitable radical of a heterocyclic ring system of the formula IV is a radical of a heterocycle from among the group below:
pyrrolidine (A); piperidine (B); tetrahydroisoquinoline (C); decahydroisoquinoline (D); octahydroindole (E); octahydrocyclopental[b]pyrrole (F); 2-aza-bicyclo[2.2.2]octane (G); 2-azabicyclo[2.2.1]heptane (H); 2-azaspiro[4.5]decane (I); 2-azaspiro[4.4]nonane (J); spiro[(bicyclo[2.2.1]heptane)-2,3-pyrrolidine] (K); spiro[(bicyclo[2.2.2]octane)-2,3-pyrrolidine] (L); 2-azatricyclo[4.3.0.1$^{6,9}$]decane (M); decahydrocyclohepta[b]pyrrole (N); octahydroisoindole (O); octahydrocyclopenta[c]pyrrole (P); 2,33a,4,5,7a-hexahydroindole (Q); tetrahydrothiazole (R); 2-azabicyclo[3.1.0]-hexane (S); all the above may or may not be substituted.

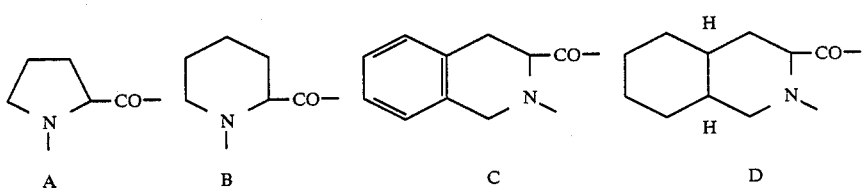

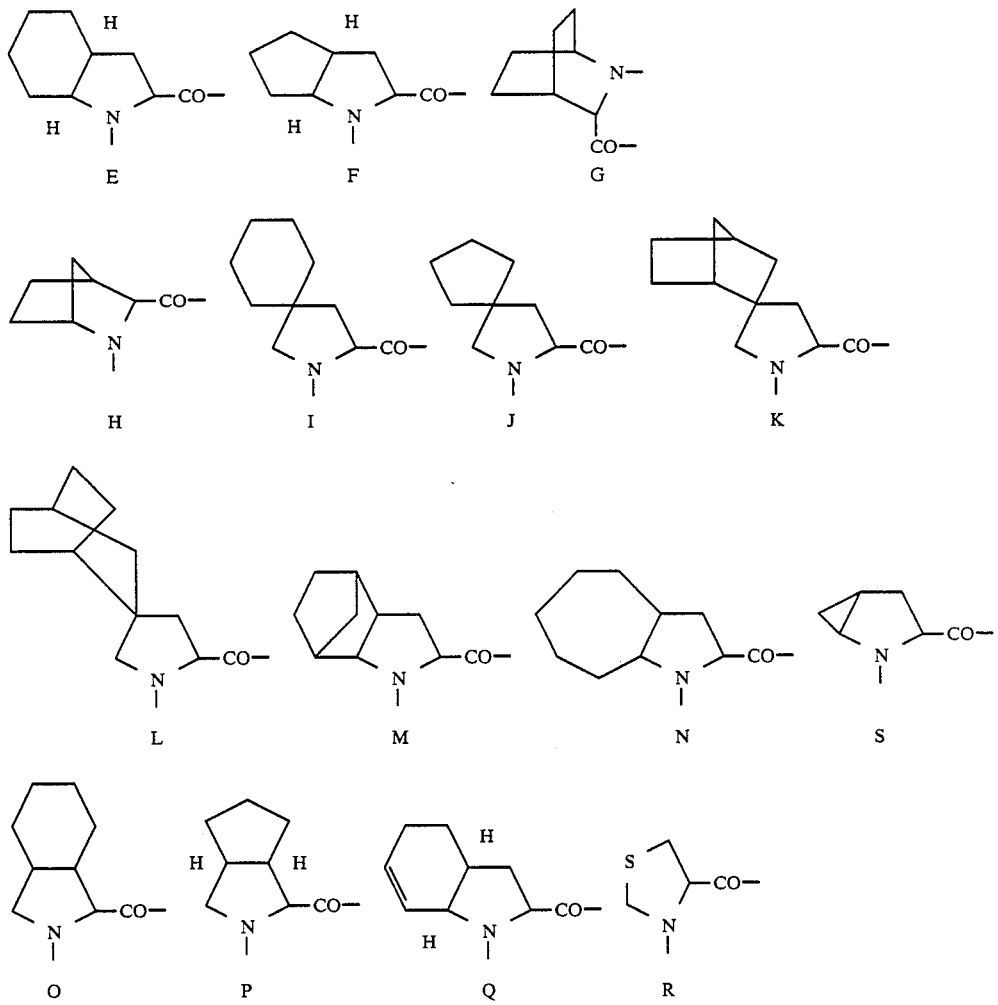

The heterocycles on which abovementioned radicals are based are known, for example, from U.S. Pat. Nos. 4,344,949, 4,374,847, 4,350,704, EP-A 50 800, EP-A 31 741, EP-A 51 020, EP-A 49 658, EP-A 49 605, EP-A 29 488, EP-A 46 953, EP-A 52 870, DE-A 32 26 768, DE-A 31 51 690, DE-A 32 10 496, DE-A 32 11 397, DE-A 32 11 676, DE-A 32 27 055, DE-A 32 42 151, DE-A 32 46 503 and DE-A 32 46 757.

Y is tert.-butyl or a glycosyl radical which is protected by protective groups customary in carbohydrate chemistry, partially protected or unprotected and which is derived from a glycopyranose, glycofuranose or an oligosaccharide.

Protected glycosyl radicals are prerred. The linkage of the glycosyl radicals to the serine radical can be both α- and β-glycosidic.

Y may, for example, be a glucofuranosyl or glucopyranosyl radical which is derived from naturally occurring aldetetroses, aldopentoses, aldohexoses, ketopentoses, deoxyaldoses, aminoaldoses and oligosaccharides such as di-and trisaccharides, and stereoisomers thereof.

The glycosyl radicals Y are in particular derived from natural D- or L-monosaccharides which occur in microorganisms, plants, animals or humans, such as ribose (Rib), arabinose (Ara), xylose (Xyl), Lyxose (Lyx), allose (All), altrose (Alt), glucose (Glc), mannose (Man), gulose (Gul), idose (Ido), glactose (sic) (Gal), talose (Tal), erythose (Ery), threose (Thr), psicose (Psi), fructose (Fru), sorbose (Sor), tagatose (Tag), xylulose (Xyu), fucose (Fuc), rhamnose (Rha), olivose (Oli), oliose (Olo), mycarose (Myc), rhodosamine (RN), N-acetyl-glucosamine (GlcNAc), N-acetylgalactosamine (GalNAc), N-acetyl-mannosamine (ManNAc), or disaccharides such as maltose (MaL), lactose (Lac), cellobiose (Cel), gentiobiose (Gen), N-acetyl-lactosamine (LacNAc), chitobiose (Chit), β-galactopyranosyl-(1,3)-N-acetylgalactosamine and β-galactopyranosyl-(1,4)-N-acetyl-glucosamine, and the synthetic derivatives thereof, such as 2-deoxy-, 2-amino, 2-acetamido- or 2-halogeno-, preferably bromo- and iodo-, sugars.

Protective groups customary in carbohydrate chemistry are understood as meaning, for example, the $(C_1-C_{10})$-acyl protective groups such as $(C_1-C_6)$-alkanoyl (e.g. acetyl, trichloroacetyl, trifluoroacetyl), benzoyl or p-nitrobenzoyl, and optionally modified methyl, methyloxymethyl, benzyl, tetrahydropyranyl, benzylidene, isopropylidene or trityl group, the acyl protective groups, in particular the acetyl (Ac) group, being preferred here.

The peptides of the formula I which are preferred are those in which X denotes $(C_1-C_{12})$-alkanecarbonyl or $(C_3-C_8)$-cycloalkanecarbonyl, each of which is optionally branched in the α-position and optionally monosubstituted in the ω-position by amino or guanidino, or represents Ser, Thr, Pro or Leu, each in their L- or D-configuration, or Ser-Ser, Thr-Thr, Ser-Thr, Pro-Ser, Pro-Thr, Thr-Pro or Ser-Pro, preferably Ser-Ser, wherein each amino acid is in its L- or D-configuration, and the N-terminal amino group of the amino acid or of the dipeptide residue being free or acylated by $(C_1-C_5)$-alkoxycarbonyl, $(C_6-C_{12})$-aryloxycarbonyl, $(C_7-C_{13})$-aralkyloxycarbonyl, $(C_1-C_6)$-alkanoyl, $(C_7-C_{13})$-aroyl, arginyl, lysyl, ε-aminocaproyl or arginyl-arginyl;

A denotes Phe or an L-2-thienylalanine residue, preferably Phe;

B denotes Arg or Lys;

C denotes Ile, Phe, Leu, Val or an L-2-thienylalanine residue;

N' denotes Asp, Glu, Gln, Asn, Leu, Ile, Trp, Asp(OBu$^t$), Glu(OBu$^t$), Glu(OBzl) or a 2-thienylalanine residue, preferably Asp, Glu or Leu, wherein each of the amino acids is in their L- or D-configuration;

E denotes Gln, Thr, or Pro;

F denotes Ser, Thr or Ala, preferably Ser or Ala, each in their L- or D-configuration;

G denotes Gly, Ala or D-Ala, and

Z represents a residue of the formula II, in which

H denotes Asn, Ser, Pro or Thr, preferably Pro, Thr or Asn, each in their L- or D-form;

I denotes Ser, Thr, Ala or Ser(Bu$^t$), preferably Ser, each in their L- or D-form;

J denotes Phe or a L-2-thienylalanine residue, preferably Phe;

K denotes Arg, Lys, Orn or a bond;

L denotes Tyr or a bond;

M denotes Arg—OH, Arg—NH$_2$, OR, NH$_2$, NHR', Gly—Lys—Arg—OH or Glu—Lys—Arg—NH$_2$;

R denotes unbranched $(C_1-C_6)$-alkyl, and

R' denotes $-[CH_2]_n-NH_2$ or $-[CH_2]_n-NH-C(NH)NH_2$, n being an integer and representing 3-8, with the proviso that peptides of the formula III and their salts.

Particularly preferred peptides are those of the formula I in which

X denotes Ser or Ser-Ser, wherein each Ser is in the L- or D-configuration, and the N-terminal amino group of the amino acid or dipeptide residue being free or being acylated by arginyl-arginyl or ε-aminocaproyl;

A denotes Phe;

B denoets Arg or Lys,

C denotes Ile, Leu, Val or an L-2-thienylalanine residue;

N' denotes Asp, Gln, Leu, Ile, Asp(OBu$^t$), Glu(OBU$^t$), Tyr(Bu$^t$) or Tyr(Me);

E denotes Gln, Thr or Pro;

F denotes Ser or Ala, each in their L- or D-configuration;

G denotes Gly, Ala or D-Ala, and

Z represents the residue of the formula II in which

H denotes Asn, Pro or Thr, each in their L- or D-form;

I denotes Ser, Thr or Ala, each in their L- or D-form;

J denotes Phe or a 2-thienylalanine residue;

K denotes Arg, Lys or a bond;

L denotes Tyr, Tyr(Bu$^t$) or a bond;

M denotes OH, NH$_2$, NHR', Gly-Lys-Arg-OH or Gly-Lys—Arg—NH$_2$, and

R' denotes $-[CH_2]2-NH_2$ or $-[CH_2]_n-NHC(NH)NH_2$, n being an integer and representing 3-8; and their physiologically tolerated salts, an exception being made of peptides of the formula III and their salts.

Unless otherwise specified in the individual case, alkyl can be straight-chain or branched. A corresponding statement applies to radicals derived therefrom, such as alkoxy, aralkyl or alkanoyl.

$C_6-C_{12}$-aryl preferably denotes phenyl, naphthyl or biphenylyl. Radicals derived therefrom, such as aryloxy, aralkyl or aroyl, are to be formulated correspondingly. Unless otherwise specified, the abbreviation of an amino acid residue without a stereo descriptor represents the residue in the L form (cf. Schroder, Lubke, The Peptides, Volume I, New York 1965, pages xiii--xxix).

Particularly suitable salts are alkali metal or alkaline earth metal salts, salts with physiologically tolerated amines and salts with inorganic or organic acids such as, for example, HCl, HBr, H$_2$SO$_4$, maleic acid and fumaric acid. The peptides according to the invention are analogs of ANF (atrial natriuretic factor) which is a peptide which is formed in the atrium of mammalian hearts and has natriuretic, diuretic and vasoactive effects (Currie et al. Science 223, 67 1985; Kangawa, Matsuo, Biochem. Biophys. Res. Commun. 118, 131 1084). The modifications according to the invention allow the effects of ANF to be intensified or specifically altered. Thus, for example, it is possible to exert a positive effect on the duration of action and the profile of action of the natriuretic properties, or to repress the vasoactive effect or even to obtain the opposite effect. Furthermore, the peptides according to the invention have immunomodulating properties which have not yet been described for peptides isolated from the atria of mammalian hearts.

The following peptides according to the invention are of very particular interest:

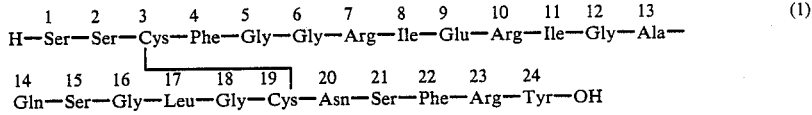
(1)

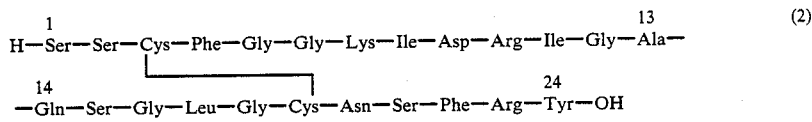
(2)

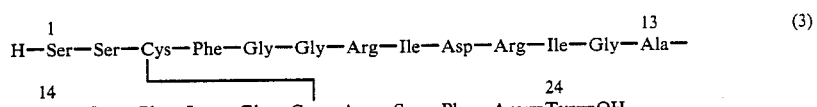
(3)

```
                1                                                    13          (4)
        H—D—Ser—Ser—Cys—Phe—Gly—Gly—Arg—Ile—Asp—Arg—Ile—Gly—Ala—
                        |                                                       |
       14                                      24
      —Gln—Ser—Gly—Leu—Gly—Cys—Asn—Ser—Phe—Arg—Tyr—OH 1                                                    13          (5)
        H—Ser—D—Ser—Cys—Phe—Gly—Gly—Arg—Ile—Asp—Arg—Ile—Gly—Ala—
                        |                                                       |
       14                                      24
      —Gln—Ser—Gly—Leu—Gly—Cys—Asn—Ser—Phe—Arg—Tyr—OH 1                                                    13          (6)
        H—Ser—Ser—Cys—Phe—Gly—Gly—Arg—Ile—Asp—Arg—Ile—Gly—Ala—
                      |                                                         |
       14                                      24
      —Gln—Ser—Gly—Leu—Gly—Cys—San—D—Ser—Phe—Arg—Tyr—OH 1                                                    13          (7)
        H—Ser—Ser—Cys—Phe—Gly—Gly—Arg—Ile—Asp—Arg—Ile—Gly—Ala—
                      |                                                         |
       14                                      24
      —Gln—D—Ala—Gly—Leu—Gly—Cys—Asn—Ser—Phe—Arg—Tyr—OH 1                                                    13          (8)
        H—Ser—Ser—Cys—Phe—Gly—Gly—Arg—Ile—Asp—Arg—Ile—Gly—Ala—
                      |                                                         |
       14                                      24
      —Gln—Ser—D—Ala—Leu—Gly—Cys—Asn—Ser—Phe—Arg—Tyr—OH 1                                                    13          (9)
        H—Ser—Ser—Cys—Phe—Gly—Gly—Arg—Ile—Asp—Arg—Ile—Ile—Gly—Ala—
                      |                                                         |
       14                                      24
      —Gln—Ser—Gly—Leu—Gly—Cys—Thr—Ser—Phe—Arg—Tyr—OH 1                                                    13         (10)
        H—Ser—Ser—Cys—Phe—Gly—Gly—Arg—Ile—Asp—Leu—Ile—Gly—Ala—
                      |                                                         |
       14                                      24
      —Gln—Ser—Gly—Leu—Gly—Cys—Asn—Ser—Phe—Arg—Tyr—OH 1                                                    13         (11)
        H—Ser—Ser—Cys—Phe—Gly—Gly—Arg—Ile—Asp—Lys—Ile—Gly—Ala—
                      |                                                         |
       14                                      24
      —Gln—Ser—Gly—Leu—Gly—Cys—Asn—Ser—Phe—Arg—Tyr—OH 1                                                    13         (12)
        H—Ser—Ser—Cys—Phe—Gly—Gly—Arg—Ile—Asp—Arg—Ile—Gly—Ala—
                      |                                                         |
       14                                      23
      —Gln—Ser—Gly—Leu—Gly—Cys—Asn—Ser—Phe—Lys—OH 1                                                    13         (13)
        H—Ser—Ser—Cys—Phe—Gly—Gly—Arg—Ile—Asp—Arg—Ile—Gly—Ala—
                      |                                                         |
       14                                      23
      —Gln—Ser—Gly—Leu—Gly—Cys—Asn—Ser—Phe—Lys—NH2

1                                                    13         (14)
        H—Ser—Ser—Cys—Phe—Gly—Gly—Arg—Ile—Asp—Arg—Ile—Gly—Ala—
                      |                                                         |
       14                                      24
      —Gln—Ser—Gly—Leu—Gly—Cys—Pro—Ser—Phe—Arg—Tyr—OH 1                                              11        (15)
        H—Arg—Arg—Ser—Ser—Cys—Phe—Gly—Gly—Arg—Ile—Glu—Arg—Ile—
                              |                                                 |
       12                                              23
      —Gly—Ala—Gln—Ser—D—Ala—Leu—Gly—Cys—Asn—Ser—Phe—Arg—
      —Tyr—OH 1                                              11        (16)
      H—Arg—Arg—Ser—Ser—Cys—Phe—Gly—Gly—Arg—Ile—Asp—Arg—Ile—
                            |                                                   |
       12                                                              24
      —Gly—Ala—Gln—Ser—Gly—Leu—Gly—Cys—Thr—Ser—Phe—Arg—Tyr—OH
```

-continued

(17)
H—Ser—Ser—Cys—Phe—Gly—Gly—Arg—Ile—Glu—Arg—Ile—Gly—Ala—
  1                 |                                          13
—Gln—Ser—Gly—Leu—Gly—Cys—Thr—Ser—Phe—Arg—Tyr—OH
 14                       |                         24

(18)
H—Arg—Arg—Ser—Ser—Cys—Phe—Gly—Gly—Arg—Ile—Glu—Arg—Ile—
  1                     |                                      11
—Gly—Ala—Gln—Ser—Gly—Leu—Gly—Cys—Thr—Ser—Phe—Arg—Tyr—OH
 12                             |                         24

(19)
H—Arg—Arg—Ser—Ser—Cys—Phe—Gly—Gly—Arg—Ile—Asp—Arg—Ile—
  1                     |                                      11
—Gly—Ala—Pro—Ser—Gly—Leu—Gly—Cys—Asn—Ser—Phe—Arg—Tyr—OH
 12                             |                         24

(20)
H—Ser—Ser—Cys—Phe—Gly—Gly—Arg—Ile—Glu—Arg—Ile—Gly—Ala—
  1                 |                                          13
—Pro—Ser—Gly—Leu—Gly—Cys—Asn—Ser—Phe—Arg—Tyr—OH
 14                       |                         24

(21)
H—Arg—Arg—Ser—Ser—Cys—Phe—Gly—Gly—Arg—Ile—Glu—Arg—Ile—
  1                     |                                      11
—Gly—Ala—Pro—Ser—Gly—Leu—Gly—Cys—Asn—Ser—Phe—Arg—Tyr—OH
 12                             |                         24

(22)
H—Ser—Ser—Cys—Phe—Gly—Gly—Arg—Ile—Asp—Arg—Ile—Gly—
  1                 |                                     12
—Ala—Pro—Ser—Gly—Leu—Gly—Cys—Thr—Ser—Phe—Arg—Tyr—OH
 13                           |                     24

(23)
H—Arg—Arg—Ser—Ser—Cys—Phe—Gly—Gly—Arg—Ile—Asp—Arg—Ile
  1                     |                                      11
—Gly—Ala—Pro—Ser—Gly—Leu—Gly—Cys—Thr—Ser—Phe—Arg—Tyr—OH
 12                             |                         24

(24)
H—Ser—Ser—Cys—Phe—Gly—Gly—Arg—Ile—Glu—Arg—Ile—Gly—Ala
  1                 |                                          13
—Pro—Ser—Gly—Leu—Gly—Cys—Thr—Ser—Phe—Arg—Tyr—OH
 14                       |                         24

(25)
H—Arg—Arg—Ser—Ser—Cys—Phe—Gly—Gly—Arg—Ile—Glu—Arg—Ile—
  1                     |                                      11
—Gly—Ala—Pro—Ser—Gly—Leu—Gly—Cys—Thr—Ser—Phe—Arg—Tyr—OH
 12                             |                         24

(26)
H—Ser—Ser—Cys—Phe—Gly—Gly—Arg—Ile—Gly—Ala—
  1                 |                               13
—Gln—Ser—Gly—Leu—Gly—Cys—Asn—Ser—Phe—Arg—OH
 14                       |                    23

(27)
H—Ser—Ser—Cys—Phe—Gly—Gly—Arg—Ile—Glu—Arg—Ile—Gly—Ala—
  1                 |                                          13
—Gln—Ser—Gly—Leu—Gly—Cys—Asn—Ser—Phe—Arg—NH₂
 14                       |                    23

(28)
H—Arg—Arg—Ser—Ser—Cys—Phe—Gly—Gly—Arg—Ile—Glu—Arg—Ile—
  1                     |                                      11
—Gly—Ala—Gln—Ser—Gly—Leu—Gly—Cys—Asn—Ser—Phe—Phe—Arg—OH
 12                             |

(29)
H—Arg—Arg—Ser—Ser—Cys—Phe—Gly—Gly—Arg—Ile—Glu—Arg—Ile—
  1                     |                                      11
—Gly—Ala—Gln—Ser—Gly—Leu—Gly—Cys—Asn—Ser—Phe—Arg—NH₂
 12                             |                    23

-continued $$\overset{1}{\text{H—Ser—Ser—Cys—Phe—Gly—Gly—Arg—Ile—Glu—Arg—Ile—}}\overset{12}{\text{Gly—}}$$
$$\overset{13}{\text{—Ala—Gln—Ser—Gly—Leu—Gly—Cys—Thr—Ser—Phe—}}\overset{23}{\text{Arg—OH}} \quad (30)$$

$$\overset{1}{\text{H—Ser—Ser—Cys—Phe—Gly—Gly—Arg—Ile—Glu—Arg—Ile—Gly—}}\overset{13}{\text{Ala—}}$$
$$\overset{14}{\text{—Gln—Ser—Gly—Leu—Gly—Cys—Thr—Ser—Phe—}}\overset{23}{\text{Arg—NH}_2} \quad (31)$$

$$\overset{1}{\text{H—Arg—Arg—Ser—Ser—Cys—Phe—Gly—Gly—Arg—Ile—Glu—Arg—}}\overset{11}{\text{Ile—}}$$
$$\overset{12}{\text{—Gly—Ala—Gln—Ser—Gly—Leu—Gly—Cys—Thr—Ser—Phe—}}\overset{23}{\text{Arg—OH}} \quad (32)$$

$$\overset{1}{\text{H—Arg—Arg—Ser—Ser—Cys—Phe—Gly—Gly—Arg—Ile—Glu—Arg—}}\overset{11}{\text{Ile—}}$$
$$\overset{12}{\text{—Gly—Ala—Gln—Ser—Gly—Leu—Gly—Cys—Thr—Ser—Phe—}}\overset{23}{\text{Arg—NH}_2} \quad (33)$$

$$\overset{1}{\text{H—Ser—Ser—Cys—Phe—Gly—Gly—Arg—Ile—Glu—Arg—Ile—Gly—}}\overset{13}{\text{Ala—}}$$
$$\overset{14}{\text{—Gln—Ser—Gly—Leu—Gly—Cys—Asn—Ser—Phe—Arg—Tyr—Gly—}}\overset{26}{\text{Lys—}}$$
$$\overset{27}{\text{—Arg—OH}} \quad (34)$$

$$\overset{1}{\text{H—Ser—Ser—Cys—Phe—Gly—Gly—Arg—Ile—Asp—Arg—Ile—Gly—}}\overset{13}{\text{Ala—}}$$
$$\overset{14}{\text{—Gln—Ser—Gly—Leu—Gly—Cys—Asn—Ser—Phe—Arg—Tyr—Gly—}}\overset{26}{\text{Lys—}}$$
$$\overset{27}{\text{—Arg—OH}} \quad (35)$$

$$\overset{1}{\text{H—Ser—Ser—Cys—Phe—Gly—Gly—Arg—Ile—Asp—Arg—Ile—Gly—}}\overset{13}{\text{Ala—}}$$
$$\overset{14}{\text{—Gln—Ser—Gly—Leu—Gly—Cys—Thr—Ser—Phe—Arg—Tyr—Gly—}}\overset{26}{\text{Lys—}}$$
$$\overset{27}{\text{—Arg—OH}} \quad (36)$$

$$\overset{1}{\text{—H—Ser—Ser—Cys—Phe—Gly—Gly—Arg—Ile—Glu—Arg—Ile—Gly—}}\overset{13}{\text{Ala—}}$$
$$\overset{14}{\text{—Gln—Ser—Gly—Leu—Gly—Cys—Thr—Ser—Phe—Arg—Tyr—Gly—}}\overset{26}{\text{Lys—}}$$
$$\overset{27}{\text{—Arg—OH}} \quad (37)$$

$$\overset{1}{\text{H—Ser—Ser—Cys—Phe—Gly—Gly—Arg—Ile—Asp—Arg—Ile—}}\overset{12}{\text{Gly—}}$$
$$\overset{13}{\text{—Ala—Pro—Ser—Gly—Leu—Gly—Cys—Asn—Ser—Phe—Arg—Tyr—}}\overset{25}{\text{Gly—}}$$
$$\overset{26}{\text{—Lys—Arg—OH}} \quad (38)$$

$$\overset{1}{\text{H—Ser—Ser—Cys—Phe—Gly—Gly—Arg—Ile—Glu—Arg—Ile—Gly—}}\overset{13}{\text{Ala—}}$$
$$\overset{14}{\text{—Pro—Ser—Gly—Leu—Gly—Cys—Asn—Ser—Phe—Arg—Tyr—Gly—}}\overset{26}{\text{Lys—}}$$
$$\overset{27}{\text{—Arg—OH}} \quad (39)$$

$$\overset{1}{\text{H—Ser—Ser—Cys—Phe—Gly—Arg—Ile—Glu—Arg—Ile—Gly—}}\overset{13}{\text{Ala—}}$$
$$\overset{14}{\text{—Pro—Ser—Gly—Leu—Gly—Cys—Thr—Ser—Phe—Arg—Tyr—Gly—}}\overset{26}{\text{Lys—}}$$
$$\overset{27}{\text{—Arg—OH}} \quad (40)$$

-continued

(41)
```
      1                                          11
H—Arg—Arg—Ser—Ser—Cys—Phe—Gly—Gly—Arg—Ile—Glu—Arg—Ile—
                       |                                |
     12                                          24
—Gly—Ala—Gln—Ser—Gly—Leu—Gly—Cys—Asn—Ser—Phe—Arg—Tyr—
     25
—Gly—Lys—Arg—OH
```

(42)
```
      1                                          11
H—Arg—Arg—Ser—Ser—Cys—Phe—Gly—Gly—Arg—Ile—Asp—Arg—Ile—
                       |                                |
     12                                          24
—Gly—Ala—Gln—Ser—Gly—Leu—Gly—Cys—Asn—Ser—Phe—Arg—Tyr—
     25
—Gly—Lys—Arg—OH
```

(43)
```
      1                                          11
H—Arg—Arg—Ser—Ser—Cys—Phe—Gly—Gly—Arg—Ile—Asp—Arg—Ile—
                       |                                |
     12                                          24
—Gly—Ala—Gln—Ser—Gly—Leu—Gly—Cys—Thr—Ser—Phe—Arg—Tyr—
     25
—Gly—Lys—Arg—OH
```

(44)
```
      1                                          11
H—Arg—Arg—Ser—Ser—Cys—Phe—Gly—Gly—Arg—Ile—Glu—Arg—Ile—
                       |                                |
     12                                          24
—Gly—Ala—Gln—Ser—Gly—Leu—Gly—Cys—Thr—Ser—Phe—Arg—Tyr—
     25
—Gly—Lys—Arg—OH
```

(45)
```
      1                                          11
H—Arg—Arg—Ser—Ser—Cys—Phe—Gly—Gly—Arg—Ile—Asp—Arg—Ile—
                       |                                |
     12                                          24
—Gly—Ala—Pro—Ser—Gly—Leu—Gly—Cys—Asn—Ser—Phe—Arg—Tyr—
     25
—Gly—Lys—Arg—OH
```

(46)
```
      1                                          11
H—Arg—Arg—Ser—Ser—Cys—Phe—Gly—Gly—Arg—Ile—Glu—Arg—Ile—
                       |                                |
     12                                          24
—Gly—Ala—Pro—Ser—Gly—Leu—Gly—Cys—Asn—Ser—Phe—Arg—Tyr—
     25
—Gly—Lys—Arg—OH
```

(47)
```
      1                                          11
H—Arg—Arg—Ser—Ser—Cys—Phe—Gly—Gly—Arg—Ile—Glu—Arg—Ile—
                       |                                |
     12                                          24
—Gly—Ala—Pro—Ser—Gly—Leu—Gly—Cys—Thr—Ser—Phe—Arg—Tyr—
     25
—Gly—Lys—Arg—OH
```

(48)
```
      1                                          11
H—Arg—Arg—Ser—Ser—Cys—Phe—Gly—Gly—Arg—Ile—Asp—Arg—Ile—
                       |                                |
     12                                          24
—Gly—Ala—Thr—Ser—Gly—Leu—Gly—Cys—Asn—Ser—Phe—Arg—Tyr—OH
```

(49)
```
      1                                          11
H—Arg—Arg—Ser—Ser—Cys—Phe—Gly—Gly—Arg—Ile—Glu—Arg—Ile—
                       |                                |
     12                                          24
—Gly—Ala—Thr—Ser—Gly—Leu—Gly—Cys—Asn—Ser—Phe—Arg—Tyr—OH
```

(50)
```
      1                                          11
H—Arg—Arg—Ser—Ser—Cys—Phe—Gly—Gly—Arg—Ile—Glu—Arg—Ile—
                       |                                |
     12                                          24
—Gly—Ala—Thr—Ser—Gly—Leu—Gly—Cys—Thr—Ser—Phe—Arg—Tyr—OH
```

(51)
```
      1                                          11
H—Arg—Arg—Ser—Ser—Cys—Phe—Gly—Gly—Arg—Ile—Asp—Arg—Ile—
                       |                                |
     12                                          24
—Gly—Ala—Thr—Ser—Gly—Leu—Gly—Cys—Thr—Ser—Phe—Arg—Tyr—OH
```

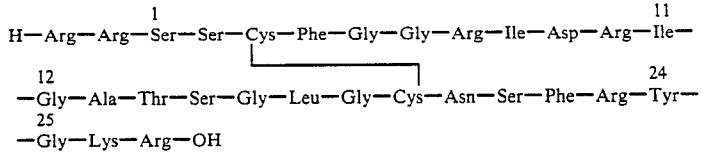

(52)

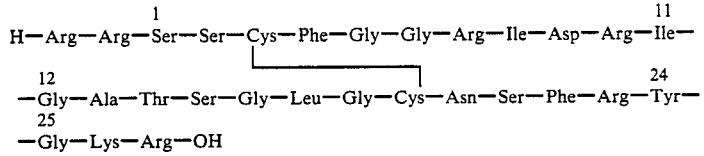

(53)

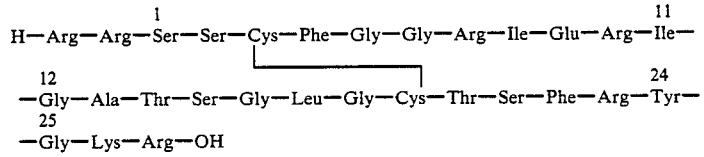

(54)

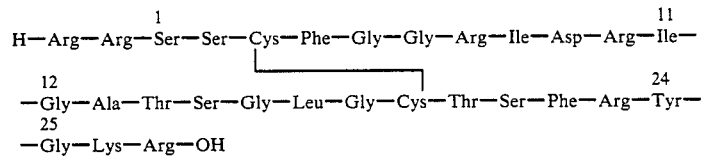

(55)

The invention also relates to a process for the preparation of peptides of the formula I, which comprises (a) reaction of a fragment with a free C-terminal carboxyl group, or its activated derivative, with an appropriate fragment with a free N-terminal amino group, or (b) stepwise synthesis of the peptide, where appropriate elimination of one or more protective groups which have been temporarily introduced to protect other groups in the compound obtained according to (a) or (b), formation of a disulfide bridge between the two Cys residues, it also being possible for the two latter measures to be carried out in the reverse sequence, and, where appropriate, conversion of the compound of the formula I thus obtained into its physiologically tolerated salt.

The peptides of the present invention were prepared by generally known methods of peptide chemistry, see, for example, Houben-Weyl, Methoden der organischen Chemi (Methods of organic chemistry), Volume 15/2, preferably by solid-phase synthesis such as described by, for example, B. Merrifield, J. Am. Chem. Soc. 85, 2149 (1963) or R. C. Sheppard Int. J. Peptide Protein Res. 21, 118 (1983), or by equivalent known methods. Urethane protective groups such as, for example, the tert.-butyloxycarbonyl(Boc) or fluorenylmethyloxycarbonyl(Fmoc) protective group are used as a α-amino protective group. If necessary to prevent side reactions or to synthesize specific peptides, the functional groups in the side chain of amino acids are additionally protected by suitable protective groups (see, for example, T. W. Greene, "Protective Groups in Organic Synthesis"), use being made primarily of Arg(Tos), Arg(Mts), Arg(Mtr), Asp(OBzl), Asp(OBu$^t$), Cys(4-MeBzl), Cys(Acm), Cys(SBut), Glu(OBzl), Glu(OBut), His(Tos), His(Fmoc), His(Dnp), His(Trt), Lys(CL-2), Lys(Boc), Met(O), Ser(Bzl), Ser(But), Thr(Bzl), Thr(Bu$^t$), Trp(Mts), Trp(CHO), Tyr(Br-Z), Tyr(Bzl) or Tyr(Bu$^t$). The solid-phase synthesis starts at the C-terminal end of the peptide with coupling of a protected amino acid to an appropriate resin. Starting materials of this type can be obtained by attaching a protected amino acid via an ester or amide bond to a polystyrene or polyacrylamide resin which has been modified with a chloromethyl, hydroxymethyl, benzhydrylamino(BHA) or methylbenzhydrylamino(MBHA) group. The resins which are used as support material are commercially available. BHA or MBHA resins are customarily used when the synthesized peptide is to contain a free amide group at the C-terminal end. If the peptide is to contain a secondary amide group at the C-terminal end, use is made of a chloromethyl- or hydroxymethyl-resin, and the elimination is carried out with the appropriate amine. If the tert.-butyl protective groups of the amino acid sidechain are to be retained in the peptide, then the synthesis is carried out with the Fmoc protective group for temporary blocking of the α-amino group of the amino acid using the methods described by, for example, R. C. Sheppard, J. Chem. Soc. Chem. Comm. 1982, 587, the guanidino group of arginine being protected by protonation with pyridinium perchlorate, and the other amino acids which are functionalized in the side chain being protected with benzyl protective groups which can be eliminated by catalytic transfer hydrogenation (A. Felix et al. J. Org. Chem. 13, 4194 (1978)) or with sodium in liquid ammonia (W. Roberts, J. Am. Chem. Soc. 76, 6203 (1954)).

After the amino protective group on the amino acid which is coupled to the resin has been eliminated with a suitable reagent such as, for example, trifluoroacetic acid in methylene chloride in the case of the Boc protective group or a 20% strength solution of piperidine in dimethylformamide in the case of the Fmoc protective group, the subsequent protected amino acids are successively coupled on in the desired sequence.

The N-terminal protected peptide resins which are produced as intermediates are deblocked by the reagents described above before linkage to the subsequent amino acid derivative.

All the possible activating reagents which are used in peptide synthesis can be used as coupling reagent, see, for example, Houben-Weyl, Methoden der organischen Chemie, Volume 15/2, but especially carbodiimides such as, for example, N,N'-dicyclohexylcarbodiimide, N,N'-diisopropylcarbodiimide or N-ethyl-N'-(3-dimethylaminopropyl)carbodiimide. In this case, the coupling can be carried out directly by addition of amino acid derivative with the activating reagent and, where appropriate, an additive which suppresses racemization, such as, for example, 1-hydroxybenzotriazole (HOBt) (W. Konig, R. Geiger, Chem. Ber. 103, 708 (1970)) or 3-hydroxy-4-oxo-3,4-dihydrobenzotriazine (HOObt) (W. Konig, R. Geiger, Chem. Ber. 103, 2054 (1970)) to the resin, or the preactivation of the amino acid derivative as the symmetrical anhydride or HOBt or HOObt ester can be carried out separately, and the solution of the activated species, in a suitable solvent, can be added to the peptide resin which is amenable to coupling.

The coupling and activation of the amino acid derivatives with one of the above-mentioned activating reagents can be carried out in dimethylformamide or methylene chloride or a mixture of the two. The activated amino acid derivative is normally used in a 1.5 to 4-fold excess. In cases where incomplete coupling occurs, the coupling reaction is repeated without previously carrying out the deblocking of the α-amino group of the peptide resin which is necessary for coupling the next amino acid. The success of the coupling reaction can be checked by the ninhydrin reaction as described by, for example, E. Kaiser et al., Anal. Biochem. 34 595 (1970). The synthesis can also be carried out automatically, for example using a model 430A peptide synthesizer supplied by Applied Biosystems, it being possible to use either the synthesis programs provided by the equipment manufacturer or those drawn up by the user himself. The latter are employed particularly when amino acid derivatives protected with the Fmoc group are used.

After the peptides have been synthesized in the manner described above, the peptide can be cleaved off the resin using reagents such as, for example, liquid hydrogen fluoride (preferred for the peptides prepared by the Boc method) or trifluoroacetic acid (preferred for the peptides synthesized by the Fmoc method). These reagents not only cleave the peptide off the resin but also cleave the other side-chain protective groups of the amino acid derivatives. In this way, except when BHA and MBHA-resins are used, the peptide is obtained in the form of the free acid. In the case of the BHA and MBHA resins, on cleavage with hydrogen fluoride the peptide is obtained as the amide. If, for example, the ethylamide is required, the peptide can be cleaved off the resin using ethylamine, the subsequent elimination of the side-chain protective groups being effected by other suitable reagents such as, for example, those mentioned above.

On cleavage off with hydrogen fluoride and trifluoroacetic acid, it is usual to add substances to capture cations, such as phenol, cresol, thiocresol, thioanisole, dimethyl sulfide, ethyl methyl sulfide or a mixture of two or more of these auxiliaries. In this case, the trifluoroacetic acid can also be used diluted by suitable solvents such as, for example, methylene chloride. If it is intended to retain the tert.-butyl and benzyl side-chain protective groups on the peptides, the peptide which has been synthesized on a specially modified support resin is cleaved off with 1% trifluoroacetic acid in methylene chloride, as described by, for example, R. C. Sheppard, J. Chem. Soc., Chem. Comm. 1982, 587. If it is intended to retain specific tert.-butyl or benzyl side-chain protective groups, a suitable combination of the methods of synthesis and cleavage off is used.

The modified support resin described by Sheppard is likewise used for the synthesis of peptides with a C-terminal amide group or an ω-amino- or ω-guanidinoalkyl group. After the synthesis, the peptide which is completely protected in the side chain is cleaved off from the resin and is then reacted in a conventional synthesis in solution with the appropriate amine or ω-aminoalkylamine or ω-guanidinoalkylamine, it being possible, where appropriate, for other functional groups which are present to be temporarily protected in a known manner.

The peptides of the present invention have been synthesized preferentially using the solid-phase technique with two general protective group tactics:

The synthesis was carried out with a model 430A automatic peptide synthesizer supplied by Applied Biosystems, using Boc or Fmoc protective groups for temporary blocking of the α-amino group. When the Boc protective group was used the synthesis cycles preprogrammed by the manufacturer of the equipment were used for the synthesis. The peptides with a free carboxylic acid at the C-terminal end were synthesized on a 4-(hydroxymethyl)phenylacetamidomethyl-polystyrene resin (R. B. Merrifield, J. Org. Chem. 43, 2845 (1978)) supplied by Applied Biosystems which was functionalized with the appropriate Boc-amino acid. An MBHA resin of the same company was used for the preparation of the peptide amides. The activating reagent used was N,N'-dicyclohexylcarbodiimide or N,N'-diisopropylcarbodiimide. The activation was effected as the symmetrical anhydride or as the HOBt ester in $CH_2CL_2$ or $CH_2CL_2$/DMF mixtures or DMF. 2-4 equivalents of activated amino acid derivative were used for the coupling. In cases where the coupling was incomplete the reaction was repeated. Linkage of the two Cys residues by a disulfide bridge is preferably effected by one of the methods described in "Perspectives in Peptide Chemistry", Karger Basel 1981, pages 31-44 or Schroder, Lubke, "The Peptides", Volume I, Academic Press, New York, London 1965, pages 235-239. Oxidation with air or $I_2$ is preferred.

When the Fmoc protective group was used for the temporary protection of the α-amino group, our own synthesis programs were entered for the synthesis with the model 430A automatic peptide synthesizer supplied by Applied Biosystems. The synthesis was carried out on a p-benzylozybenzyl alcohol-resin (S. Wang, J. Am. Chem. Soc. 95, 1328 (1973)) supplied by Bachem, which had been esterified with the appropriate amino acid by a known method (E. Atherton et al., J.C.S. Chem. Comm. 1981, 336). The amino acid derivatives were activated as HOBt esters directly in the amino acid cartridges supplied by the equipment manufacturer, by addition of a solution of diisopropylcarbodiimide in DMF to the mixture of amino acid derivative and HOBt which had previously been weighed in. The Fmoc protective group was eliminated with a 20% strength solution of piperidine in DMF in the reaction vessel. The excess of reactive amino acid derivative which was used was 1.5 to 2.5 equivalents. If the coupling was incomplete it was repeated in the same way as the Boc method.

In order to introduce the glycosyl radicals into serine or threonine the amino group and the carboxyl group must be appropriately protected beforehand. Protective groups which have proven to be particularly advantageous for this purpose are those which can be split off by catalytic hydrogenation or by means of secondary amines. In the former case these are protective groups of the benzyl type, e.g. the benzyloxycarbonyl(Z) or p-nitrobenzyloxycarbonyl radical, as amino protective groups, and the benzyl (—OBzl) or p-nitrobenzyl ester, for the carboxyl group. The 9-fluorenylmethyloxycarbonyl (Fmoc) radical can be split off with secondary amines. The use of Fmoc-L-or Fmoc-D-Ser-OBzl has proven particularly advantageous since, after glycosidation, the benzyl esters of the corresponding Fmoc-L- or Fmoc-D-Ser($R^1$)-OBzl could be cleaved off selectively by catalytic hydrogenation with retention of the Fmoc group. This is particularly surprising since recently there have been many reports that the Fmoc radical is cleaved off by catalytic hydrogenation [e.g. by R. Geiger and W. König in E. Gross and J. Meienhofer (Eds): The Peptides, 3, p. 24, Academic Press, 1981].

Two polyfunctional reactants (carbohydrate and serine or threonine) are to be linked in the synthesis of the O-glycosyl amino acid building blocks. Both must be amenable to selective blocking and unblocking. In the glycosyl component the anomeric center must be amenable to liberation and functionalization and in the amino acid component it is permissible for only the hydroxyl group required for linking to be unblocked. Depending on the type of glycosidic bond desired (1,2-cis- or 1,2-transglycosides) it is necessary to introduce protective groups suitable for blocking the hydroxyl or amino groups into the glycosyl component and to find reaction conditions for the linking step which stereoselectively leads to only one of the two possible anomers.

Both the O-glycosyl amino acid building blocks, most of which are naturally occurring and which are known from the literature, such as those described, e.g., by K. Dill et al. [Carbohydr. Res. 123 (1983) 137–144], H. Kunz ]Nach. Chem. Tech. Lab. 32 (1984) 11]and H. Paulsen [Chem. Soc. Res. 13 (1) (1984) 25–45], and the artificial O-glycosylserine and glycosylthreonine derivatives which are prepared by the glycosidation processes customary in carbohydrate chemistry such as those described by A. F. Bochkov and G. E. Zaikov [Chemistry of the O-glycosidic bond, Pergamon Press 157 (1979)], H. Paulsen [Angew. Chem. 94 (1982) 184–201]and R. R. Schmidt [Angew. Chem. 98 (1986) 213–236]or by modified glycosidation processes, are used for the preparation of the compounds of the formula I, according to the invention, which compounds contain an O-glycosyl radical. The glycosylated amino acid building blocks are introduced on the cyclize peptide.

The vasorelaxant effect of the peptides according to the invention was tested in vitro on strips of guinea-pig aorta which have previously been contracted with 25 mM KCl. The diuretic and natriuretic effects were demonstrated in vivo by i.v. administration to anesthetized rats. Atriopeptin III was used for comparison.

Thus the invention also relates to the use of the peptides of the formula I as medicines and pharmaceutical formulations which contain these peptides. Administration to humans is preferred.

The new peptides according to the invention have, individually or in combination, diuretic, salidiuretic, vasorelaxant and immunomodulating effects at a dose of 10 to 2000 picomole/kg (25 ng–5 µ/kg). For this purpose the peptides can be administered parenterally (i.v., s.c. or i.m.) in a physiologically tolerated medium.

For parenteral administration, the active compounds or their physiologically tolerated salts are converted into solutions, suspensions or emulsions, if desired using the substances customary for this purpose, such as solubilizers, emulsifiers or other auxiliaries. Examples of suitable solvents for the new active compounds and the corresponding physiologically tolerated salts are: water, physiological sodium chloride solutions or alcohols, for example ethanol, propanediol or glycerol, as well as sugar solutions, such as glucose or mannitol solutions, or a mixture of the various solvents mentioned.

It is likewise possible to administer the active compounds by implants, for example composed of polyeactide, polyglycolide, copolymers of lactic and glycolic acid or poly-3-hydroxybutyric acid, or intranasal formulations. On intranasal administration, the dose must be increased 10-fold because less is absorbed. Furthermore, the peptides can be administered in the form of their physiologically tolerated salts or metal complexes.

The invention furthermore relates to the use of compounds of the formula I in the treatment of glaucoma and/or for reducing the intraocular pressure in mammals, preferably humans, by topical or systemic administration.

For ophthalmologic use of the compounds according to the invention they are expediently incorporated into pharmaceutical products in a conventional manner. They can be converted into the customary administration forms such as solutions, ointments, emulsions or into a depot form. Where appropriate, the active compound may also be present in microencapsulated form. The products may contain compatible organic or inorganic additives, for example suspending agents, solvents, antibacterial agents, wetting agents and preservatives. Forms for topical application are preferred. Parenteral formulations can also be used. Systemic use forms are administered one to three times a day in an amount of about 25 ng–5 µ/kg. For topical application it is preferable to use solutions, ointments or opthtalmic (sic) inserts (solid inserts). Forms for topical application may contain 0.001–5 per cent by weight of the active compound. Higher or lower doses may also be used provided that they reduce the intraocular pressure. 0.01 mg–1 mg of the active compound are preferably applied to the human eye. For the preferred topical application to the eye the compounds of the formula I are administered in combination with physiologically tolerated vehicles, e.g. aqueous methylcellulose. The combination can take the form of a suspension, solution, ointment, emulsion or an Okusert. A preferred combination facilitates penetration of the active compounds into the eye. A further preferred topical application form is a combination of the compounds of the formula I with compounds such as, for example, benzalkonium chloride which facilitates penetration of the active compound into the eye. Compounds of the formula I can also be employed in combination with other antiglaucoma compounds for the treatment of glaucoma.

The topical vehicles may be organic or inorganic compounds. Typical pharmaceutical vehicles employed are aqueous solutions which are, for example, buffer systems or isotonic mixtures of water and water-miscible solvents, for example alcohols or aryl alcohols, oils, polyalkylene glycols, ethylcellulose, carboxymethylcellulose, polyvinylpyrrolidone or isopropyl myristate. Suitable buffer substances are, for example, sodium chloride, sodium borate, sodium phosphate, sodium acetate or a gluconate buffer. The topical application form may also contain non-toxic auxiliaries, such as, for example, emulsifying preservatives, crosslinking agents such as polyethylene glycols, antibacterial compounds, such as, for example, quaternary ammonium compounds, benzalkonium chloride, phenylmercury salts, benzyl alcohol, phenylethanol, triethanolamine oleate, thiosorbitol and further similar substances which are employed in topical ophthalmic formulations. The topical application forms may also be an ophthalmic insert (solid insert). For this, for example, a solid water-soluble polymer can be employed as carrier for the active compound. The polymer used may be any water-soluble non-toxic polymer, such as, for example, cellulose derivatives such as, for example, methylcellulose, sodium carboxymethylcellulose, hydroxy-$C_{1-6}$-alkylcellulose, e.g. hydroxyethylcellulose, hydroxypropylcellulose and hyroxypropylemethylcellulose, acrylic acid derivatives, such as polyacrylates, ethyl acrylates and polyacrylamides. It is furthermore possible to use, for example, gelatine, starch derivatives, alginates, pectins, polyvinyl alcohols, polyvinylpyrrolidones, polyvinyl methyl ethers, polyethylene oxides or mixtures of the various polymers. Solid inserts which are suitable for topical application are described in British Patent Application 1,524,405.

List of abbreviations:

The abbreviations used for amino acids correspond to the three-letter code customary in peptide chemistry, as is described in, for example, Europ. J. Biochem. 138, 9 (1984). Other abbreviations which are used are listed below.

Acm: acetamidomethyl
Boc: tert.-butyloxycarbonyl
But: ter.-butyl
Bzl: benzyl
Cl-Z: 4-chlorobenzyloxycarbonyl
DMF: dimethylformamide
Dnp: 2,4-dinitrophenyl
Fmoc: 9-fluoroenylmethyloxycarbonyl
Me: methyl
4-Mebzl: 4-methylbenzyl
Mtr: 4-methoxy-2,3,6-trimethylphenylsulfonyl
Mts: mesitylene-2-sulfonyl
TFA: trifluoroacetic acid
Tcs: 4-methylphenylsulfonyl
Trt: trityl.
ε-Ahx: ε-aminohexanoyl
AOC: cis, endo-azabicyclo[3.3.0]octane-3-S-carbonyl The examples which follow are intended to illustrate the preferred methods for the solid-phase synthesis of the peptides according to the invention, but without restricting the invention to them.

EXAMPLE 1:

Synthesis of the ANF derivative which has natriuretic and diuretic activity and vasoactivity and the formula tained 0.5 mmol of tyrosine. For the synthesis, use was made of the following amino acid derivatives which were likewise supplied by Applied Biosystems, and which were already weighed out in 2-mmol amounts in cartridges for use in the peptide synthesizer: Boc-Arg(Tos)-OH, Boc-Phe-OH, Boc-Ser(Bzl)-OH, Boc-Asn-OH, Boc-Cys(4-MeBzl)-OH, Boc-Gly-OH, Boc-Leu-OH, Boc-Gln-OH, Boc-Ala-OH, Boc-Ile-OH, Boc-Glu(OBzl)-OH. The synthesis made use of the programs provided by the equipment manufacturer, one example being listed below.

(1) 65% trifluoroacetic acid/$CH_2Cl_2$, 5 ml, 2 min
(2) 65% trifluoroacetic acid/$CH_2Cl_2$, 5 ml, 15 min
(3) Washing with $CH_2Cl_2$ (3×10 ml)
(4) Washing with 10% diisopropylethylamine in DMF (2×10 ml)
(5) Washing with DMF (3×10 ml)
(6) Coupling of the amino acid derivative which has previously been activated as the symmetrical anhydride or HOBt ester (30–15 min), repeating if necessary where coupling is incomplete.
(7) Washing with $CH_2Cl_2$ (6×10 ml).

After the synthesis was complete, the peptide-resin was dried in vacuo over molecular sieves. To cleave the peptide off from the resin, 1 g of peptide-resin was weighed, together with 0.5 g of p-cresol and 0.5 g of p-thiocresol, into the reaction vessel of an HF apparatus supplied by Protein Research Foundation, Minowa, Osaka, Japan, and, after the apparatus had been evacuated, about 10 ml of liquid HF was distilled in at the temperature of dry ice. Reaction was then allowed to take place at 0° C. for 1 h, and thereafter the excess HF was cautiously removed by distillation in vacuo. The remaining yellow-red resin/peptide mixture was washed several times with ethyl acetate and dry ether to remove the cation-capture agent. After drying, the peptide was extracted from the resin using 30% strength aqueous acetic acid, and the resulting crude peptide solution was freeze-dried. The freeze-dried crude peptide was separated on Sephadex$^{(R)}$ G25 superfine from any cation-capture agent which was still present, using 1N acetic acid, and the peptide-containing fractions were worked up further. For this purpose, the crude peptide was dissolved in trifluoroethanol and reduced with a 5-fold excess of tri-n-butylphosphine overnight. After removal of the solvent in vacuo, the residue was extracted several times with acetic acid (sic), and the crude peptide obtained as the sediment was briefly dried and immediately oxidized with $I_2$. 0.5 mmol of peptide was dissolved in 50 ml of 90% strength acetic acid, and this solution was rapidly added dropwise to an efficiently stirred solution of 0.5 mmol of $I_2$ and 1 mmol of sodium acetate in 450 ml of 80% strength aqueous acetic acid. The solution was then stirred for 10 min, decolorized by addition of 0.1 N aqueous ascorbic acid, concentrated to about 10 ml and immediately freed of salts on Sephadex$^{(R)}$ G25 superfine with 1N aqueous $$\text{H}-\text{Ser}-\text{Ser}-\overset{|}{\text{Cys}}-\text{Phe}-\text{Gly}-\text{Gly}-\text{Arg}-\text{Ile}-\text{Glu}-\text{Arg}-\text{Ile}-\text{Gly}-\overset{13}{\text{Ala}}-$$
$$-\overset{14}{\text{Gln}}-\text{Ser}-\text{Gly}-\text{Leu}-\text{Gly}-\overset{|}{\text{Cys}}-\text{Asn}-\text{Ser}-\text{Phe}-\text{Arg}-\overset{24}{\text{Tyr}}-\text{OH}$$

was carried out with a model 430A automatic peptide synthesizer supplied by Applied Biosytems by the Boc method on a 4-(hydroxymethyl)phenylacetamidomethylpolystyrene resin, supplied by Applied Biosystems, which was substituted by Boc-Tyr(Br-Z)-OH and conacetic acid as eluent. The fractions containing the peptide were combined and freeze-dried. The purity was checked by HPLC on Vydac$^{(R)}C_{18}$ and Vydac$^{(R)}C_4$ columns with a gradient of acetonitrile in 0.1% strength aqueous trifluoroacetic acid. For final purification, preparative HPLC separation was carried out on the same support material with the same eluent mixture.

EXAMPLE 2:

The peptide which has natriuretic, diuretic and vasorelaxant activity and the formula

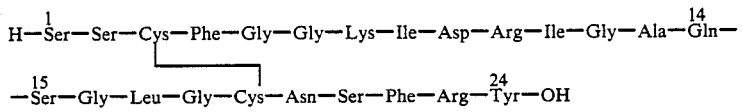

was synthesized stepwise with a model 430A peptide synthesizer supplied by Applied Biosystems using the Fmoc method on a p-benzylozybenzyl alcohol-resin which was supplied by Bachem and was esterified with Fmoc-Tyr(Bu$^t$)—OH (loading 0.40 mmol/g of resin). 1 g of this resin was used, and the synthesis was carried out with the synthesis programs modified for the Fmoc method.

The following amino acid derivatives were used: Fmoc-Arg(Mtr)-OH, Fmoc-Phe-OH, Fmoc-Ser(Bu$^t$)-OH, Fmoc-Asn-OH, Fmoc-Cys(Acm)-OH, Fmoc-Gly-OH, Fmoc-Leu-OH, Fmoc-Gln-OH, Fmoc-Ala-OH, Fmoc-Ile-OH, Fmoc-Asp(OBu$^t$)-OH and Fmoc-Lys(Boc)-OH. 1 mmol of each amino acid derivative was weighed, together with 1.5–2.5 equivalents of HOBt, into the synthesizer cartridges. The amino acids were activated directly in the cartridges by dissolving in 4 ml of DMF and addition of a 0.55 molar solution of N,N′-diisopropylcarbodiimide in DMF (2 ml). A typical synthesis cycle is listed below:

(1) Elimination of the Fmoc group with 20 % piperidine in DMF (2×8 ml, 10 min each)
(2) Washing with DMF (6×8 ml of DMF each time)
(3) Coupling of the amino acid derivative which had previously been activated in the cartridge as the HOBt ester (25-45 min), repeating if necessary where coupling was incomplete
(4) Washing with DMF (6×8 ml of DMF each time).

After the synthesis was complete, first the Fmoc protective group was eliminated from the peptide-resin by treatment with 20% piperidine in DMF, and the resin was thoroughly washed with DMF and shrunk by treatment several times with isopropanol and methyl tert.-butyl ether. After drying under high vacuum, the peptide was cleaved off from the resin by stirring with a mixture of trifluoroacetic acid/CH$_2$Cl$_2$/phenol (70:30:5) at room temperature for 4 h. Any remaining protective groups were eliminated by subsequent treatment with trifluoroacetic acid/phenol/dimethyl sulfide (90:5:5). The resin was then removed by filtration and washed with cleavage solution, and the filtrate was concentrated in vacuo. The cation-capture agents were removed by stirring with ethyl acetate several times. After drying under high vacuum, the crude peptide was separated from any cation-capture agent and traces of trifluoroacetic acid which were still present on Sephadex$^{(R)}$ G25 superfine with 1N aqueous acetic acid. The peptide-containing fractions were freeze-dried and then worked up further. The oxidative elimination of the Acm protective groups on the cysteine was carried out by the method of Kamber et al. Helv. Chim. Acta 63, 899 (1980) in 90% strength aqueous acetic acid with a 50-fold excess of I$_2$ and a reaction time of 15 min. The crude peptide thus obtained was freed of salts and finally purified as described in Example 1.

EXAMPLE 3:

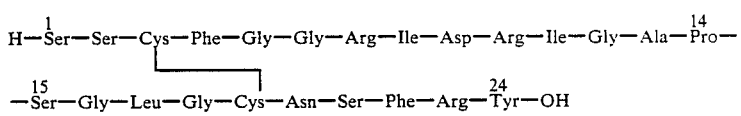

Synthesis as described in Example 1 on Boc-Tyr(Br-Z)-OCH$_2$-PAM-resin supplied by Applied Biosystems.

EXAMPLE 4:

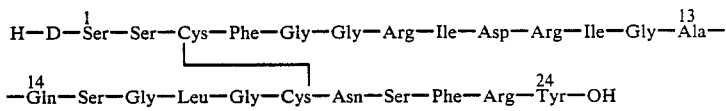

Synthesis as described in Example 1 on Boc-Tyr(Br-Z)-OCH$_2$-PAM-resin supplied by Applied Biosystems.

EXAMPLE 5:

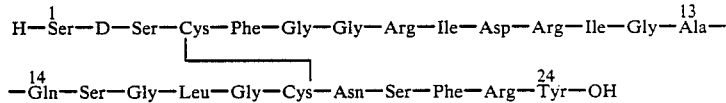

Synthesis as described in Example 1 on Box-Tyr(Br-Z)-OCH$_2$-PAM-resin supplied by Applied Biosystems.

EXAMPLE 6:

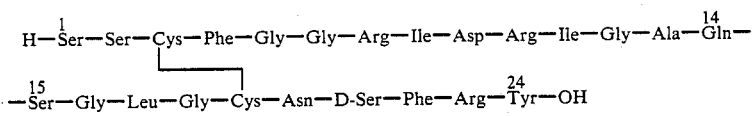

Synthesis as described in Example 1 on Boc-Tyr(Br-Z)-OCH$_2$-PAM-resin supplied by Applied Biosystems.

EXAMPLE 7:

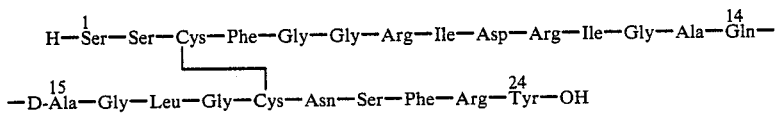

Synthesis as described in Example 1 on Boc-Tyr(Br-Z)-OCH$_2$-PAM-resin supplied by Applied Biosystems.

EXAMPLE 8:

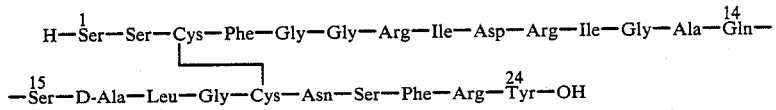

Synthesis as described in Example 1 on Boc-Tyr(Br-Z)-OCH$_2$-PAM-resin supplied by Applied Biosystems.

EXAMPLE 9:

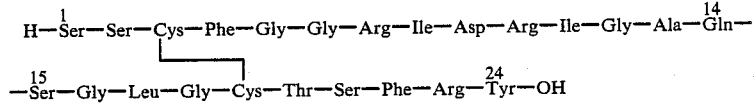

Synthesis as described in Example 1 on Boc-Tyr(Br-Z)-OCH$_2$-PAM-resin supplied by Applied Biosystems.

EXAMPLE 10:

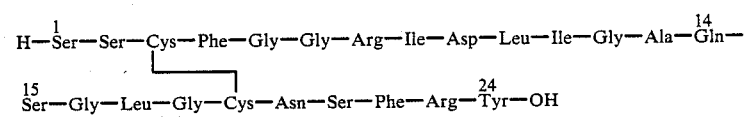

Synthesis as described in Example 1 on Boc-Tyr(Br-Z)-OCH$_2$-PAM-resin supplied by Applied Biosystems.

EXAMPLE 11:

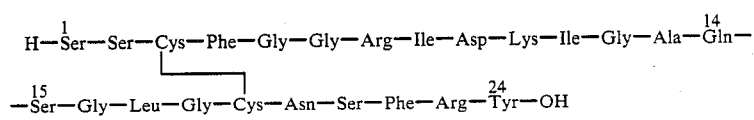

Synthesis as described in Example 2 on p-benzyloxy-benzyl alcohol-resin supplied by Bachem and esterified with Fmoc-Tyr(Bu$^t$)-OH.

EXAMPLE 12:

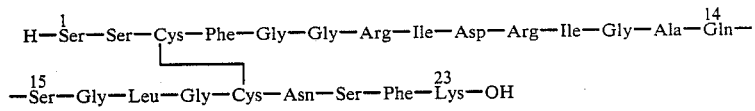

Synthesis as described in Example 1 on Boc-Lys(Cl-Z)-OCH$_2$-PAM-resin supplied by Applied Biosystems.

EXAMPLE 13:

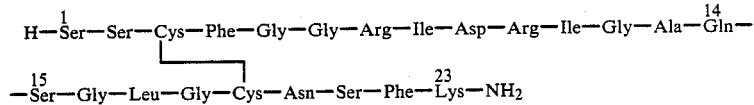

Synthesis as described in Example 1 on MBHA-resin supplied by Applied Biosystems, the first amino acid coupled to the resin being Boc-Lys(Cl-Z)-OH.

EXAMPLE 14:

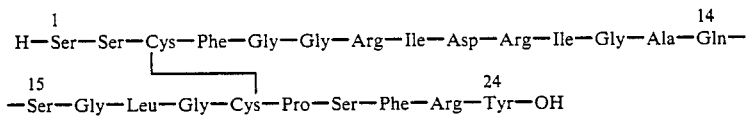

Synthesis as described in Example 2 on p-benzyloxybenzyl alcohol-resin supplied by Bachem and esterified with Fmoc-Tyr(Bu$^t$)-OH.

EXAMPLE 15:

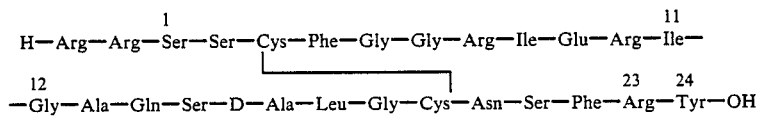

Synthesis as described in Example 2 on p-benzyloxybenzyl alcohol-resin suplied by Bachem and esterified with Fmoc-Tyr(Bu$^t$)-OH.

EXAMPLE 16:

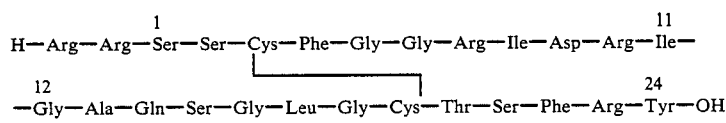

Synthesis as described in Example 2 on p-benzyloxybenzyl alcohol-resin supplied by Bachem and esterified with Fmoc-Tyr(Bu$^t$)-OH.

EXAMPLE 17:

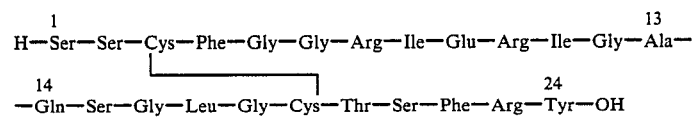

Synthesis as described in Example 2 on p-benzyloxybenzyl alcohol-resin supplied by Bachem and esterified with Fmoc-Tyr(Bu$^t$)-OH.

EXAMPLE 18:

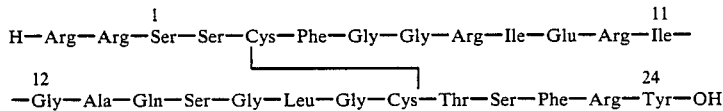

Synthesis as described in Example 2 on p-benzyloxybenzyl alcohol-resin supplied by Bachem and esterified with Fmoc-Tyr(Bu$^1$)-OH.

EXAMPLE 19:

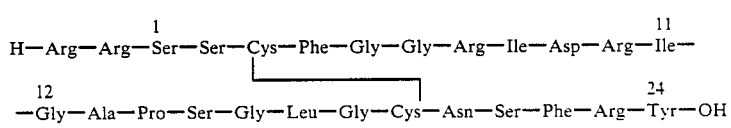

Synthesis as described in Example 2 on p-benzyloxybenzyl alcohol-resin supplied by Bachem and esterified with Fmoc-Tyr(Bu$^1$)-OH.

EXAMPLE 20:

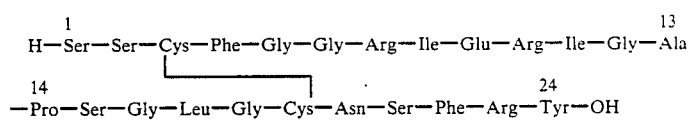

Synthesis as described in Example 2 on p-benzyloxybenzyl alcohol-resin supplied by Bachem and esterified with Fmoc-Tyr(Bu$^1$)-OH.

EXAMPLE 21:

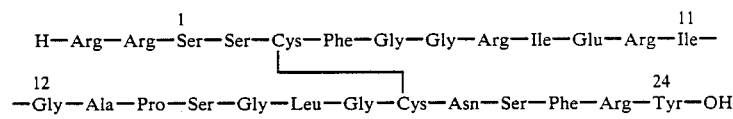

Synthesis as described in Example 2 on p-benzyloxy-benzyl alcohol-resin supplied by Bachem and esterified with Fmoc-Tyr(Bu^t)-OH.

EXAMPLE 22:

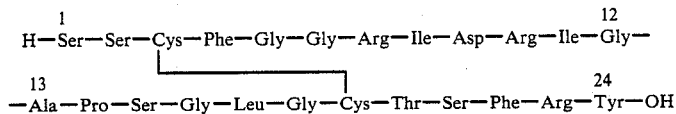

Synthesis as described in Example 2 on p-benzyloxy-benzyl alcohol-resin supplied by Bachem and esterified with Fmoc-Tyr(Bu^t)-OH.

EXAMPLE 23:

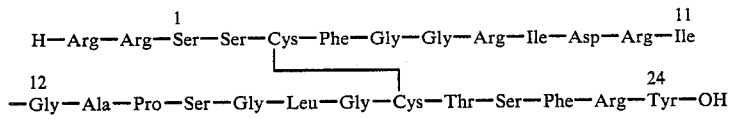

Synthesis as described in Example 2 on p-benzyloxy-benzyl alcohol-resin supplied by Bachem and esterified with Fmoc-Tyr(Bu^t)-OH.

EXAMPLE 24:

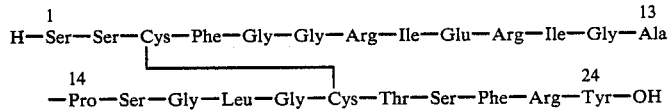

Synthesis as described in Example 2 on p-benzyloxy-benzyl alcohol-resin supplied by Bachem and esterified with Fmoc-Tyr(Bu^t)-OH.

EXAMPLE 25:

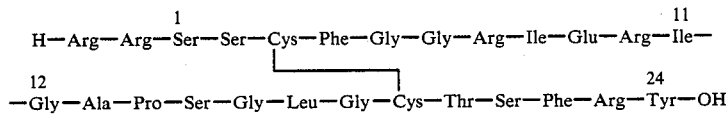

Synthesis as described in Example 2 on p-benzyloxy-benzyl alcohol-resin supplied by Bachem and esterified with Fmoc-Tyr(Bu^t)-OH.

EXAMPLE 26:

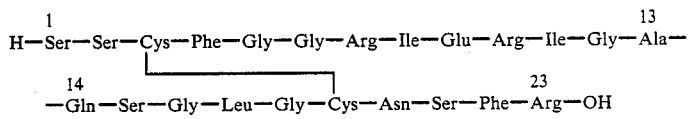

Synthesis as described in Example 2 on p-benzylozy-benzyl alcohol-resin supplied by Bachem and esterified with Fmoc-Arg(Mtr)-OH.

EXAMPLE 27:

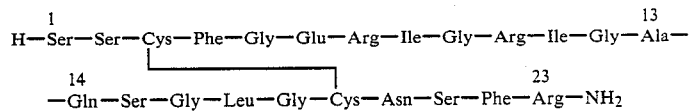

Synthesis as described in Example 1 on MBHA-resin supplied by Applied Biosystems, the first amino acid coupled to the resin being Boc-Arg(Tos)-OH.

EXAMPLE 28:

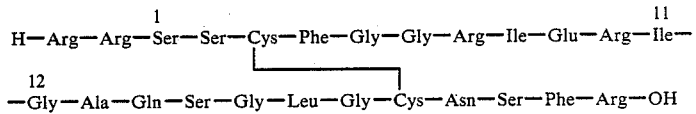

Synthesis as described in Example 2 on p-benzylozy-benzyl alcohol-resin supplied by Bachem and esterified with Fmoc-Arg(Mtr)-OH.

EXAMPLE 29:

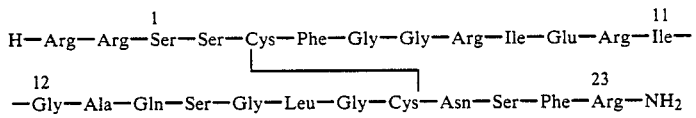

Synthesis as described in Example 1 on MBHA-resin supplied by Applied Biosystems, the first amino acid coupled to the resin being Boc-Arg(Tos)-OH.

EXAMPLE 30:

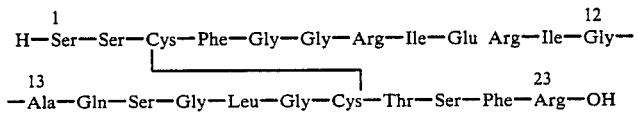

Synthesis as described in Example 2 on p-benzylozy-benzyl alcohol-resin supplied by Bachem and esterified with Fmoc-Arg(Mtr)-OH.

EXAMPLE 31:

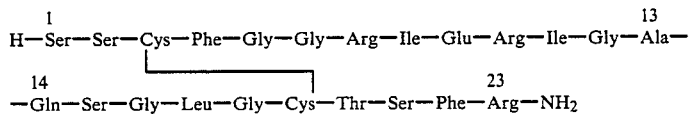

Synthesis as described in Example 1 on MBHA-resin supplied by Applied Biosystems, the first amino acid coupled to the resin being Boc-Arg(Tos)-OH.

EXAMPLE 32:

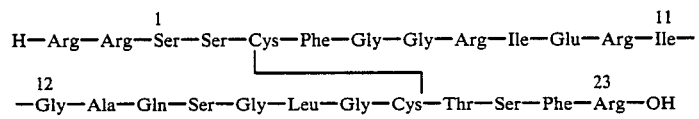

Synthesis as described in Example 2 on p-benzylozy-benzyl alcohol-resin supplied by Bachem and esterified with Fmoc-Arg(Mtr)-OH.

EXAMPLE 33:

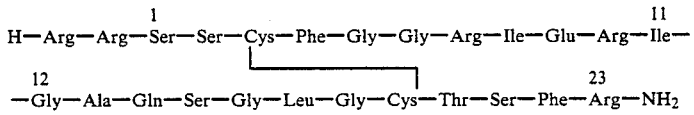

Synthesis as described in Example 1 on MBHA-resin supplied by Applied Biosystems, the first amino acid coupled to the resin being Boc-Arg(Tos)-OH.

EXAMPLE 34:

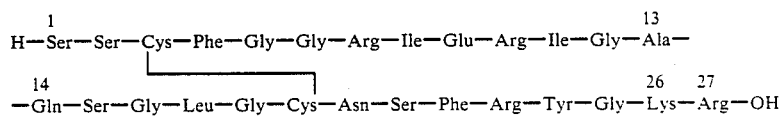

Synthesis as described in Example 2 on p-benzyloxy-benzyl alcohol-resin supplied by Bachem and esterified with Fmoc-Arg(Mtr)-OH.

EXAMPLE 35:

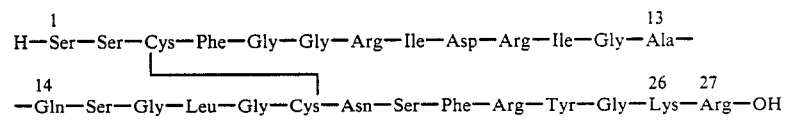

Synthesis as described in Example 2 on p-benzyloxy-benzyl alcohol-resin supplied by Bachem and esterified with Fmoc-Arg(Mtr)-OH.

EXAMPLE 36:

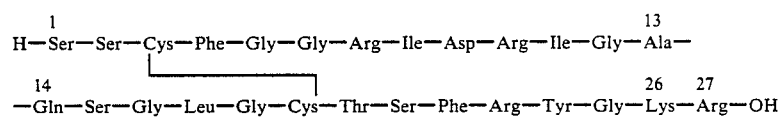

Synthesis as described in Example 2 on p-benzylozy-benzyl alcohol-resin supplied by Bachem and esterified with Fmoc-Arg(Mtr)-OH.

EXAMPLE 37:

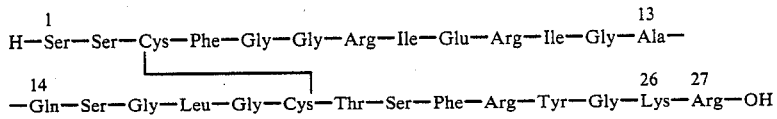

Synthesis as described in Example 2 on p-benzylozy-benzyl alcohol-resin supplied by Bachem and esterified with Fmoc-Arg(Mtr)-OH.

EXAMPLE 38:

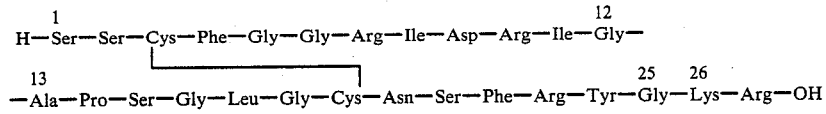

Synthesis as described in Example 2 on p-benzylozy-benzyl alcohol-resin supplied by Bachem and esterified with Fmoc-Arg(Mtr)-OH.

EXAMPLE 39:

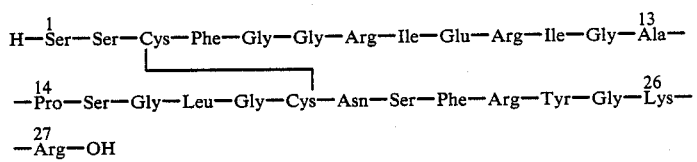

Synthesis as described in Example 2 on p-benzyloxy-benzyl alcohol-resin supplied by Bachem and esterified with Fmoc-Arg(Mtr)-OH.

EXAMPLE 40:

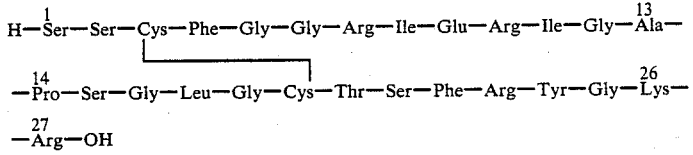

Synthesis as described in Example 2 on p-benzyloxy-benzyl alcohol-resin supplied by Bachem and esterified with Fmoc-Arg(Mtr)-OH.

EXAMPLE 41:

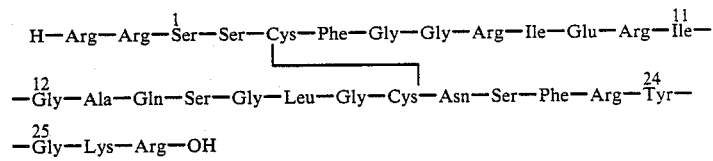

Synthesis as described in Example 2 on p-benzyloxy-benzyl alcohol-resin supplied by Bachem and esterified with Fmoc-Arg(Mtr)-OH.

EXAMPLE 42:

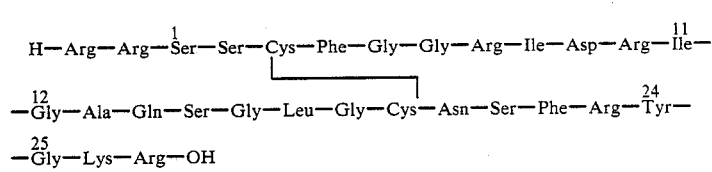

Synthesis as described in Example 2 on p-benzyloxy-benzyl alcohol-resin supplied by Bachem and esterified with Fmoc-Arg(Mtr)-OH.

EXAMPLE 43:

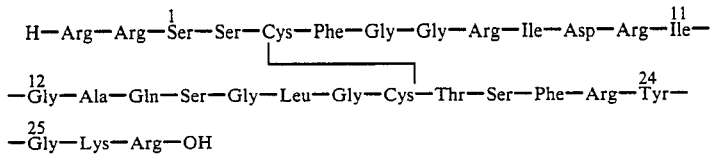

Synthesis as described in Example 2 on p-benzyloxy-benzyl alcohol-resin supplied by Bachem and esterified with Fmoc-Arg(Mtr)-OH.

EXAMPLE 44:

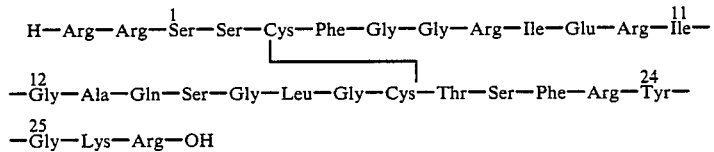

Synthesis as described in Example 2 on p-benzyloxy-benzyl alcohol-resin supplied by Bachem and esterified with Fmoc-Arg(Mtr)-OH.

EXAMPLE 45:

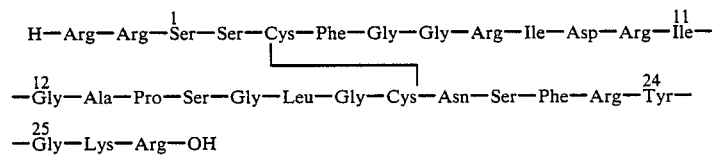

Synthesis as described in Example 2 on p-benzyloxy-benzyl alcohol-resin supplied by Bachem and esterified with Fmox-Arg(Mtr)-OH.

EXAMPLE 46:

H—Arg—Arg—Ser—Ser—Cys—Phe—Gly—Gly—Arg—Ile—Glu—Arg—Ile—
—Gly—Ala—Pro—Ser—Gly—Leu—Gly—Cys—Asn—Ser—Phe—Arg—Tyr—
—Gly—Lys—Arg—OH

Synthesis as described in Example 2 on p-benzyloxy-benzyl alcohol-resin supplied by Bachem and esterified with Fmoc-Arg(Mtr)-OH.

EXAMPLE 47:

H—Arg—Arg—Ser—Ser—Cys—Phe—Gly—Gly—Arg—Ile—Glu—Arg—Ile—
—Gly—Ala—Pro—Ser—Gly—Leu—Gly—Cys—Thr—Ser—Phe—Arg—Tyr—
—Gly—Lys—Arg—OH

Synthesis as described in Example 2 on p-benzyloxy-benzyl alcohol-resin supplied by Bachem and esterified with Fmoc-Arg(Mtr)-OH.

EXAMPLE 48:

H—Arg—Arg—Ser—Ser—Cys—Phe—Gly—Gly—Arg—Ile—Asp—Arg—Ile—
—Gly—Ala—Thr—Ser—Gly—Leu—Gly—Cys—Asn—Ser—Phe—Arg—Tyr—OH

Synthesis as described in Example 2 on esterified p-benzyloxybenzyl alcohol-resin.

EXAMPLE 49:

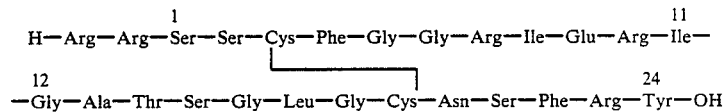

Synthesis as described in Example 2 on esterified p-benzyloxybenzyl alcohol-resin.

EXAMPLE 50:

```
         1                                              11
H—Arg—Arg—Ser—Ser—Cys—Phe—Gly—Gly—Arg—Ile—Glu—Arg—Ile—
 12                                             24
—Gly—Ala—Thr—Ser—Gly—Leu—Gly—Cys—Thr—Ser—Phe—Arg—Tyr—OH
```

Synthesis as described in Example 2 on esterified p-benzyloxybenzyl alcohol-resin.

EXAMPLE 51

```
         1                                              11
H—Arg—Arg—Ser—Ser—Cys—Phe—Gly—Gly—Arg—Ile—Asp—Arg—Ile—
 12                                             24
—Gly—Ala—Thr—Ser—Gly—Leu—Gly—Cys—Tyr—Ser—Phe—Arg—Tyr—OH
```

Synthesis as described in Example 2 on esterified p-benzyloxybenzyl alcohol-resin.

EXAMPLE 52:

```
         1                                              11
H—Arg—Arg—Ser—Ser—Cys—Phe—Gly—Gly—Arg—Ile—Asp—Arg—Ile—
 12                                             24
—Gly—Ala—Thr—Ser—Gly—Leu—Gly—Cys—Asn—Ser—Phe—Arg—Tyr—
 25
—Gly—Lys—Arg—OH
```

Synthesis as described in Example 2 on esterified p-benzyloxybenzyl alcohol-resin.

EXAMPLE 53

```
         1                                              11
H—Arg—Arg—Ser—Ser—Cys—Phe—Gly—Gly—Arg—Ile—Glu—Arg—Ile—
 12                                             24
—Gly—Ala—Thr—Ser—Gly—Leu—Gly—Cys—Asn—Ser—Phe—Arg—Tyr—
 25
—Gly—Lys—Arg—OH
```

Synthesis as described in Example 2 on esterified p-benzyloxybenzyl alcohol-resin.

EXAMPLE 54:

```
         1                                              11
H—Arg—Arg—Ser—Ser—Cys—Phe—Gly—Gly—Arg—Ile—Glu—Arg—Ile—
 12                                             24
—Gly—Ala—Thr—Ser—Gly—Leu—Gly—Cys—Thr—Ser—Phe—Arg—Tyr—
 25
—Gly—Lys—Arg—OH
```

Synthesis as described in Example 2 on esterified p-benzyloxybenzyl alcohol-resin.

EXAMPLE 55:

```
         1                                              11
H—Arg—Arg—Ser—Ser—Cys—Phe—Gly—Gly—Arg—Ile—Asp—Arg—Ile—
 12                                             24
—Gly—Ala—Thr—Ser—Gly—Leu—Gly—Cys—Thr—Ser—Phe—Arg—Tyr—
 25
—Gly—Lys—Arg—OH
```

Synthesis as described in Example 2 on esterified p-benzyloxybenzyl alcohol-resin.

EXAMPLE 56:

```
         1                                              13
H—Ser—Ser—Cys—Phe—Gly—Gly—Arg—Ile—Glu—Arg—Ile—Gly—Ala—
 14
—Thr—Ser—Gly—Leu—Gly—Cys—Pro—Ser—Phe—Arg—Tyr—OH
```

Synthesis as described in Example 2 on esterified p-benzyloxybenzyl alcohol-resin.

EXAMPLE 57:

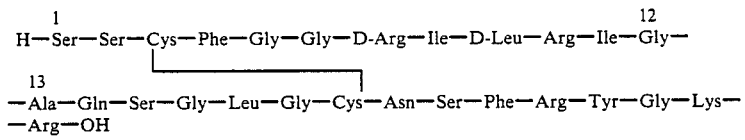

Synthesis as described in Example 2 on esterified p-benzyloxybenzyl alcohol-resin.

EXAMPLE 58:

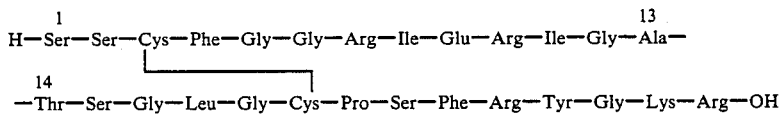

Synthesis as described in Example 2 on esterified p-benzyloxybenzyl alcohol-resin.

EXAMPLE 59:

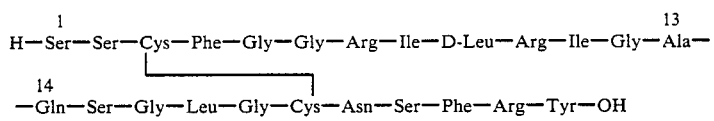

Synthesis as described in Example 2 on esterified p-benzyloxybenzyl alcohol-resin.

EXAMPLE 60:

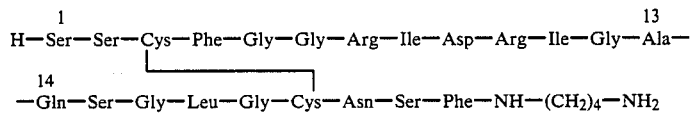

First, the peptide was synthesized by a method similar to that described in Example 2 on a p-benzyloxybenzyl alcohol-resin which was supplied by Bachem and was esterified with Fmoc-Phe-OH, using Fmoc-Arg(TOS)-OH, Fmoc-Phe-OH, Fmoc-Ser(Bzl)-OH, Fmoc-Asn-OH, Fmoc-Cys(Acm)-OH, Fmoc-Gly-OH, Fmoc-Leu-OH, Fmoc-Gln-OH, Fmoc-Ala-OH, Fmoc-Ile-OH and Fmoc-Asp(Obzl)-OH. The protected peptide is then cleaved off from the resin with a mixture of trifluoroacetic acid/CH$_2$Cl$_2$/phenol (70:30:5) as described in Example 2.

After stirring several times with ethyl acetate to remove the cation-capture agents, the dried crude peptide in DMF is coupled with Boc-NH-(CH$_2$)$_4$-NH$_2$ using diisopropylcarbodiimide/HOBt. Reaction overnight is followed by stripping off the solvent and extracting the residue by stirring with ethyl acetate. The crude peptide is treated with HF, as described in Example 1, to cleave off the protective groups and the crude peptide obtained is cyclized by means of oxidation. Working-up and purification are carried out as described in Example 1.

EXAMPLE 61:

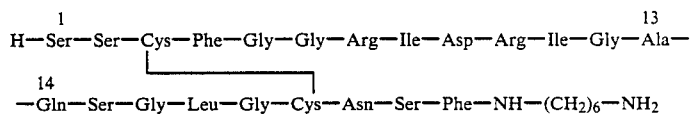

Synthesis in analogy with the procedure described in Example 60.

EXAMPLE 62:

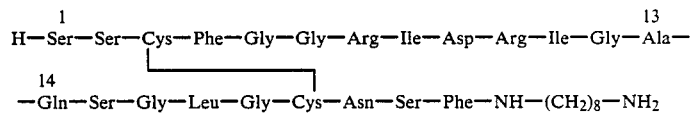

Synthesis in analogy with the procedure described in Example 60.

EXAMPLE 63:

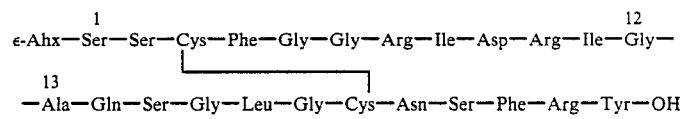

Synthesis as described in Example 2 on esterified p-benzyloxybenzyl alcohol-resin.

EXAMPLE 64:

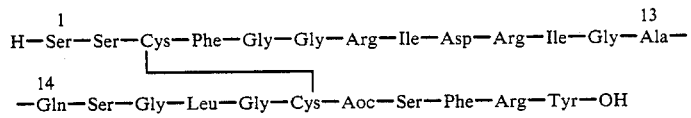

Synthesis as described in Example 2 on esterified p-benzyloxybenzyl alcohol-resin.

EXAMPLE 65:

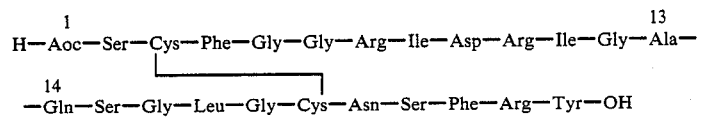

Synthesis as described in Example 2 on esterified p-benzyloxybenzyl alcohol-resin.

EXAMPLE 66:

```
   2                                                               15
H—Iva—Cys—Phe—Gly—Gly—Arg—Ile—Asp—Arg—Ile—Gly—Ala—Gln—Ser—
       |                                                           
      16                                                           
  —Gly—Leu—Gly—Cys—Asn—Ser—Phe—Arg—Tyr—OH
```

Synthesis as described in Example 2 on esterified p-benzyloxybenzyl alcohol-resin.

EXAMPLE 67:

```
   2                                                               15
H—Aoc—Cys—Phe—Gly—Gly—Arg—Ile—Asp—Arg—Ile—Gly—Ala—Gln—Ser—
       |                                                           
      16                                                           
  —Gly—Leu—Gly—Cys—Asn—Ser—Phe—Arg—Tyr—OH
```

Synthesis as described in Example 2 on esterified p-benzyloxybenzyl alcohol-resin.

EXAMPLE 68:

Synthesis as described in Example 2 on esterified p-benzyloxybenzyl alcohol-resin.

EXAMPLE 69:

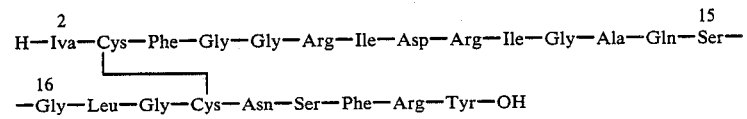

Synthesis as described in Example 2 on esterified p-benzyloxybenzyl alcohol-resin.

EXAMPLE 70:

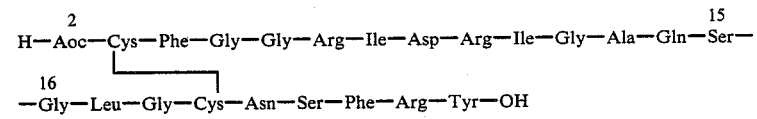

Synthesis as described in Example 2 on esterified p-benzyloxybenzyl alcohol-resin.

EXAMPLE 71:

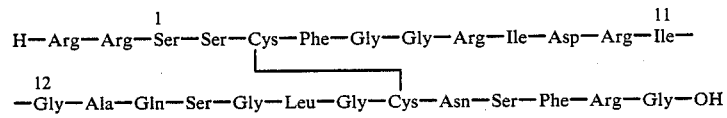

Synthesis as described in Example 2 on esterified p-benzyloxybenzyl alcohol-resin.

EXAMPLE 72:

```
      1                                                     11
H—Arg—Arg—Ser—Ser—Cys—Phe—Gly—Gly—Arg—Ile—Asp—Arg—Ile—
                    |                                       
     12                                                     
  —Gly—Ala—Gln—Ser—Gly—Leu—Gly—Cys—Asn—Ser—Phe—Arg—Gly—OH
```

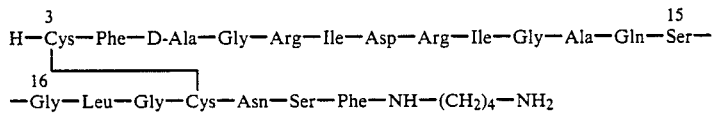

Synthesis in analogy with the procedure described in Example 60.

The peptides were characterized by amino acid analysis. The peptides were hydrolyzed with 6N hydrochloric acid for 12 hours at 120° C. Cysteine was obtained as a mixture of cysteine and cysteic acid and was contained in all the peptides.

| Amino acid analyses | | | | | | | | | | | |
|---|---|---|---|---|---|---|---|---|---|---|---|
| Example | 1 | 2 | 3 | 4 | 5 | 6 | 7 | 8 | 9 | 10 | 11 |
| Asp: | 1.02 | 2.02 | 2.00 | 1.98 | 1.85 | 1.87 | 1.92 | 1.95 | 0.98 | 2.04 | 2.05 |
| Thr: | | | | | | | | | 0.88 | | |
| Ser: | 3.35 | 3.56 | 3.67 | 3.38 | 3.12 | 3.26 | 2.18 | 3.28 | 3.32 | 3.46 | 3.21 |
| Glu: | 2.02 | 1.01 | | 1.03 | 1.09 | 0.98 | 0.98 | 1.07 | 1.03 | 1.01 | 1.02 |
| Pro: | | | | | | | | | | | |
| Gly: | 4.98 | 5.01 | 5.02 | 5.00 | 4.88 | 5.01 | 4.98 | 3.95 | 5.02 | 5.03 | 5.06 |
| Ala: | 1.08 | 1.05 | 1.02 | 1.11 | 1.05 | 1.08 | 2.11 | 2.02 | 1.12 | 1.07 | 1.13 |
| Ile: | 1.90 | 1.95 | 1.92 | 1.88 | 1.86 | 1.87 | 1.90 | 1.81 | 1.86 | 1.92 | 1.86 |
| Leu: | 1.04 | 1.03 | 0.99 | 1.07 | 1.10 | 1.01 | 1.02 | 1.10 | 1.07 | 2.13 | 1.09 |
| Tyr: | 0.88 | 0.82 | 0.78 | 0.80 | 0.81 | 0.83 | 0.83 | 0.85 | 0.82 | 0.80 | 0.79 |
| Phe: | 2.00 | 2.00 | 2.00 | 2.00 | 2.00 | 2.00 | 2.00 | 2.00 | 2.00 | 2.00 | 2.00 |
| Lys: | | 1.02 | | | | | | | | | 0.97 |
| Arg: | 2.98 | 1.92 | 2.99 | 3.01 | 2.85 | 2.83 | 2.91 | 2.86 | 2.92 | | 1.89 |
| Example | 12 | 13 | 14 | 15 | 16 | 17 | 18 | 19 | 20 | 21 | 22 |
| Asp: | 1.97 | 2.02 | 0.99 | 1.01 | 1.02 | | | 1.98 | 1.00 | 1.02 | 0.98 |
| Thr: | | | | | 0.79 | 0.82 | 0.86 | | | | 0.80 |
| Ser: | 3.48 | 3.39 | 3.25 | 3 38 | 3.22 | 3.42 | 3.40 | 3.45 | 3.38 | 3.41 | 3.34 |
| Glu: | 1.02 | 1.04 | 1.00 | 2.05 | 1.03 | 2.02 | 1.98 | | 1.02 | 0.99 | |
| Pro: | | | 1.01 | | | | | 0.98 | 0.96 | 1.03 | 0.97 |
| Gly: | 5.03 | 4.98 | 5.02 | 3.98 | 4.97 | 5.01 | 4.99 | 4.96 | 5.02 | 5.01 | 4.99 |
| Ala: | 1.09 | 1.07 | 1.12 | 2.08 | 1.04 | 1.07 | 1.06 | 1.10 | 1.08 | 1.15 | 1.06 |
| Ile: | 1.77 | 1.81 | 1.86 | 1.91 | 1.93 | 1.89 | 1.92 | 1.87 | 1.88 | 1.90 | 1.93 |
| Leu: | 1.09 | 1.01 | 1.03 | 1.02 | 0.99 | 1.01 | 1.02 | 1.00 | 0.98 | 1.01 | 1.03 |
| Tyr: | | | 0.73 | 0.82 | 0.78 | 0.80 | 0.82 | 0.78 | 0.76 | 0.79 | 0.79 |
| Phe: | 2.00 | 2.00 | 2.00 | 2.00 | 2.00 | 2.00 | 2.00 | 2.00 | 2.00 | 2.00 | 2.00 |
| Lys: | 1.03 | 0.98 | | | | | | | | | |
| Arg: | 1.85 | 1.86 | 2.82 | 4.77 | 4.69 | 2.84 | 4.71 | 4.73 | 2.81 | 4.69 | 2.86 |
| Example | 23 | 24 | 25 | 26 | 27 | 28 | 29 | 30 | 31 | 32 | 33 |
| Asp: | 1.01 | | | 0.98 | 0.97 | 0.99 | 1.02 | | | | |
| Thr: | 0.80 | 0.78 | 0.82 | | | | | 0.81 | 0.79 | 0.76 | 0.84 |
| Ser: | 3.41 | 3.34 | 3.39 | 3.46 | 3.51 | 3.38 | 3.49 | 3.28 | 3.15 | 3.28 | 3.51 |
| Glu: | | 1.02 | 1.03 | 2.04 | 2.06 | 2.02 | 1.99 | 2.12 | 2.03 | 2.05 | 2.01 |
| Pro: | 0.96 | 1.02 | 0.98 | | | | | | | | |
| Gly: | 4.99 | 5.02 | 4.98 | 4.97 | 5.01 | 5.00 | 5.03 | 5.01 | 5.03 | 4.99 | 5.04 |
| Ala: | 1.03 | 1.07 | 1.06 | 1.04 | 1.02 | 1.05 | 1.02 | 1.09 | 1.10 | 1.08 | 1.03 |
| Ile: | 1.89 | 1.89 | 1.92 | 1.83 | 1.91 | 1.78 | 1.83 | 1.85 | 1.86 | 1.87 | 1.90 |
| Leu: | 0.97 | 1.02 | 1.03 | 1.01 | 1.00 | 1.08 | 1.07 | 1.03 | 1.04 | 1.01 | 1.01 |
| Tyr: | 0.77 | 0.83 | 0.81 | | | | | | | | |
| Phe: | 2.00 | 2.00 | 2.00 | 2.00 | 2.00 | 2.00 | 2.00 | 2.00 | 2.00 | 2.00 | 2.00 |
| Lys: | | | | | | | | | | | |
| Arg: | 4.67 | 2.81 | 4.72 | 2.78 | 2.81 | 4.77 | 4.79 | 4.69 | 2.76 | 4.73 | 4.75 |
| Example | 34 | 35 | 36 | 37 | 38 | 39 | 40 | 41 | 42 | 43 | 44 |
| Asp: | 1.02 | 1.01 | 0.99 | | 1.99 | 1.02 | | 1.03 | 2.04 | 1.02 | |
| Thr: | | | 0.83 | 0.88 | | | 0.90 | | | 0.85 | 0.88 |
| Ser: | 3.42 | 3.39 | 3.27 | 3.41 | 3.32 | 3.44 | 3.38 | 3.40 | 3.36 | 3.29 | 3.37 |
| Glu: | 2.04 | 1.01 | 1.03 | 1.98 | | 1.03 | 1.01 | 2.05 | 0.99 | 1.01 | 2.03 |
| Pro: | | | | | 0.95 | 1.02 | 1.01 | | | | |
| Gly: | 6.07 | 6.04 | 6.05 | 6.06 | 6.02 | 6.09 | 6.05 | 6.03 | 6.07 | 6.02 | 6.04 |
| Ala: | 1.03 | 1.05 | 1.08 | 1.04 | 1.03 | 1.03 | 1.05 | 1.07 | 1.04 | 1.09 | 1.06 |
| Ile: | 1.87 | 1.83 | 1.85 | 1.88 | 1.78 | 1.80 | 1.83 | 1.85 | 1.89 | 1.89 | 1.82 |
| Leu: | 1.05 | 1.03 | 1.04 | 1.01 | 1.09 | 1.08 | 1.03 | 1.03 | 1.04 | 0.99 | 1.05 |
| Tyr: | 0.78 | 0.82 | 0.88 | 0.84 | 0.79 | 0.70 | 0.81 | 0.78 | 0.76 | 0.82 | 0.83 |
| Phe: | 2.00 | 2.00 | 2.00 | 2.00 | 2.00 | 2.00 | 2.00 | 2.00 | 2.00 | 2.00 | 2.00 |
| Lys: | 1.03 | 0.98 | 1.08 | 1.02 | 1.07 | 1.06 | 1.09 | 1.06 | 1.08 | 1.03 | 1.01 |
| Arg: | 3.72 | 3.78 | 3.80 | 3.79 | 3.74 | 3.85 | 3.83 | 5.76 | 5.69 | 5.72 | 5.68 |
| Example | 45 | 46 | 47 | 48 | 49 | 50 | 51 | 52 | 53 | 54 | 55 |
| Asp: | 2.04 | 1.03 | | 2.01 | 1.00 | | 1.02 | 1.98 | 1.01 | | 0.98 |
| Thr: | | | 0.83 | 0.85 | 0.79 | 1.63 | 1.58 | 0.89 | 0.86 | 1.62 | 1.08 |
| Ser: | 3.39 | 3.42 | 3.51 | 3.48 | 3.50 | 3.41 | 3.22 | 3.35 | 3.38 | 3.40 | 3.37 |
| Glu: | | 1.03 | 1.02 | | 1.05 | 1.03 | | | 1.01 | 2.04 | 1.03 |
| Pro: | 0.98 | 1.02 | 1.01 | | | | | | | | |
| Gly: | 6.05 | 6.03 | 6.07 | 5.02 | 5.04 | 5.01 | 5.07 | 6.05 | 6.08 | 6.07 | 6.01 |
| Ala: | 1.07 | 1.05 | 1.04 | 1.05 | 1.08 | 1.07 | 1.09 | 1.05 | 1.03 | 1.04 | 1.07 |

| -continued | | | | | | | | | | |
|---|---|---|---|---|---|---|---|---|---|---|
| Amino acid analyses | | | | | | | | | | |
| Ile: | 1.86 | 1.85 | 1.79 | 1.81 | 1.84 | 1.87 | 1.79 | 1.82 | 1.85 | 1.83 | 1.80 |
| Leu: | 1.02 | 1.01 | 1.03 | 1.01 | 1.01 | 1.00 | 1.04 | 1.02 | 1.01 | 1.02 | 1.04 |
| Tyr: | 0.69 | 0.75 | 0.81 | 0.78 | 0.79 | 0.76 | 0.84 | 0.72 | 0.75 | 0.89 | 0.79 |
| Phe: | 2.00 | 2.00 | 2.00 | 2.00 | 2.00 | 2.00 | 2.00 | 2.00 | 2.00 | 2.00 | 2.00 |
| Lys: | 1.03 | 0.99 | 1.02 | | | | | 1.01 | 1.02 | 1.01 | 1.03 |
| Arg: | 5.72 | 5.78 | 5.82 | 4.73 | 4.76 | 4.69 | 4.71 | 5.79 | 5.81 | 5.69 | 5.72 |

| Example | 56 | 57 | 58 | 59 | 60 | 61 | 62 | 63 | 64 | 65 | 66 |
|---|---|---|---|---|---|---|---|---|---|---|---|
| Asp: | | 0.99 | | 1.01 | 2.03 | 1.98 | 2.01 | 2.00 | 0.99 | 2.01 | 2.01 |
| Thr: | 0.82 | | 0.79 | | | | | | | | |
| Ser: | 3.41 | 3.45 | 3.35 | 3.40 | 3.38 | 3.36 | 3.41 | 3.34 | 3.31 | 2.60 | 1.71 |
| Glu: | 1.03 | 1.01 | 1.04 | 1.02 | 0.99 | 1.01 | 1.03 | 1.02 | 1.00 | 1.03 | 1.01 |
| Pro: | 0.98 | | 1.01 | | | | | | | | |
| Gly: | 5.04 | 6.02 | 6.05 | 5.03 | 5.02 | 5.03 | 5.06 | 5.01 | 5.03 | 5.02 | 5.04 |
| Ala: | 1.07 | 1.08 | 1.07 | 1.09 | 1.06 | 1.08 | 1.07 | 1.07 | 1.09 | 1.06 | 1.08 |
| Ile: | 1.86 | 1.91 | 1.92 | 1.92 | 1.88 | 1.90 | 1.87 | 1.89 | 1.84 | 1.88 | 1.86 |
| Leu: | 1.02 | 1.03 | 1.03 | 1.05 | 1.05 | 1.04 | 1.06 | 1.05 | 1.07 | 1.08 | 1.06 |
| Tyr: | 0.78 | 0.82 | 0.80 | 0.79 | | | | 0.76 | 0.78 | 0.81 | 0.80 |
| Phe: | 2.00 | 2.00 | 2.00 | 2.00 | 2.00 | 2.00 | 2.00 | 2.00 | 2.00 | 2.00 | 2.00 |
| Lys: | | | | | | | | | | | |
| Arg: | 2.83 | 3.75 | 3.69 | 2.81 | 1.90 | 1.86 | 1.88 | 2.78 | 2.83 | 2.80 | 2.85 |

| Example | 67 | 68 | 69 | 70 | 71 | 72 |
|---|---|---|---|---|---|---|
| Asp: | 2.03 | 2.01 | 2.02 | 2.02 | 2.00 | 2.03 |
| Thr: | | | | | | |
| Ser: | 1.69 | 3.45 | 3.41 | 3.38 | 3.37 | 1.72 |
| Glu: | 1.03 | 1.01 | 0.99 | 1.03 | 1.02 | 1.00 |
| Pro: | | | 1.01 | 0.98 | 1.01 | |
| Gly: | 5.02 | 6.04 | 5.01 | 4.98 | 3.99 | 4.03 |
| Ala: | 1.06 | 1.06 | 1.07 | | 1.08 | 2.08 |
| Ile: | 1.83 | 1.85 | 0.92 | 1.88 | 1.88 | 1.84 |
| Leu: | 1.06 | 1.08 | 1.05 | 1.09 | 1.06 | 1.08 |
| Tyr: | 0.81 | | 0.78 | 0.79 | 0.76 | |
| Phe: | 2.00 | 2.00 | 2.00 | 2.00 | 2.00 | 2.00 |
| Lys: | | | | | | |
| Arg: | 2.81 | 2.83 | 2.86 | 2.79 | 2.81 | 1.90 |

We claim:

1. A peptide of the formula I

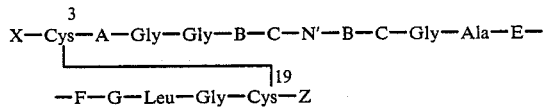

in which

X denotes $(C_1-C_{12})$-alkanecarbonyl or $(C_3-C_8)$-cycloalkanecarbonyl, each of which is optionally branched in the α-position and is optionally monosubstituted in the ω-position by amino or guanidino, or represents Ser, Thr, Ser(Y), Thr(Y), Q or Leu, in each case in their L- or D-configuration, or Ser-Ser, Thr-Thr, Ser-Thr, Q-Ser, Q-Thr, Thr-Q, Ser-Q, Ser(Y)-Ser or Ser-Ser(Y), wherein each amino acid is in its L- or D-configuration and the N-terminal amino group of the amino acid or of the dipeptide residue being free or acylated by $(C_1-C_5)$-alkoxycarbonyl, $(C_6-C_{12})$-arloxycarbonyl, $(C_7-C_{13})$-aralkyloxycarbonyl, $(C_1-C_6)$-alkanoyl, $(C_7-C_{13})$-aroyl, arginyl, lysyl, ε-aminocaproyl, arginyl-arginyl, arginyl-lysyl, lysyl-arginyl or lysyl-lysyl; A denotes Phe, Trp or an L-2-thienylalanine residue; B denotes Arg, Lys, or Orn; C denotes Ile, Met, Phe, Trp, Leu, Ser, Thr, Val, His, Pro, Asn, Ser(Bu$^t$) or an L-2-thienylalanine residue; N denotes Asp, Glu, Gln, Asn, Phe, Leu, Ile, Trp, Pro, Tyr, Ala, Asp(OBu$^t$), Asp(OBzl), Glu(OBu$^t$), Glu(OBzl), a 2-thienylalanine residue, Aad, Tyr(Bu$^t$) or Tyr(Me), wherein each of the amino acids is in their L- or D-configuration;

E denotes Gln, Thr or Pro;

F denotes Ser, Thr, Pro, Ala, Ser(Bu$^t$) or Thr(Bu$^t$), each in their L- or D-configuration;

G denotes Gly, Ala or D-Ala;

Q denotes a radical of the formula IV

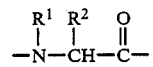 (IV)

in which $R^1$ and $R^2$, together with the atoms carrying these radicals, form a heterocyclic mono-, bi- or tri-cyclic ring system having 3 to 15 carbon atoms;

Y denotes tert.-butyl or an optionally partially or completely protected glycosyl radical; and Z represents a residue of the formula II

 (II)

in which

H denotes Asn, Ser, Q or Thr, each in their L- or D-form;

I denotes Ser, Thr, Ala, Ser(Bu$^t$), Thr(Bu$^t$) or Pro, each in their L- or D-form;

J denotes Phe, Trp, D-Phe, D-Trp or a 2-thienylalanine residue;

K denotes Arg, Lys, Orn or a bond;

L denotes Tyr, Tyr(Bu$^t$) or a bond;

M denotes Arg-OH, Arg-NH$_2$, OH, OR, NH$_2$, NHR', Gly-Lys-Arg-OH, Gly-Lys-Arg-NH$_2$ or L-argininol;

Q is as defined above;

R denotes unbranched $(C_1-C_6)$-alkyl, and

R' denotes —[CH₂]ₙ-NH₂ or —[CH₂]ₙ-NH-C(NH)NH₂, n being an integer and representing 3-8; and to its physiologically tolerated salts, with the proviso that the peptides, corresponding to the sequence of the natural ANF, of the formula III

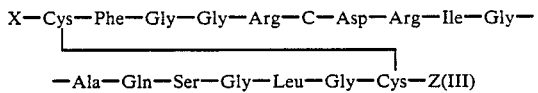

in which
X denotes Ser, Ser-Ser, Arg-Ser-Ser or Arg-Arg-Ser-Ser,
C denotes Ile or Met,
Z denotes Asn-Ser-Phe-K-L-M,
K denotes Arg or a bond,
L denotes Tyr or a bond and
M denotes OH or NH₂, and their salts are excluded.

2. A peptide of the formula I as claimed in claim 1, in which Q denotes Pro, and its physiologically tolerated salts.

3. A peptide of the formula I as claimed in claim 1, in which Y denotes tert.-butyl, and its physiologically tolerated salts.

4. A peptide of the formula I as claimed in claim 1, in which
X denotes (C₁-C₁₂)-alkanecarbonyl or (C₃-C₈)-cycloalkanecarbonyl, each of which is optionally branched in the α-position and optionally monosubstituted in the ω-position by amino or guanidino, or represents Ser, Thr, Pro or Leu, each in their L- or D-configuration, or Ser-Ser, Thr-Thr, Ser-Thr, Pro-Ser, Pro-Thr, Thr-Pro or Ser-Pro, wherein each amino acid is in its L- or D-configuration, and the N-terminal amino group of the amino acid or of the dipeptide residue being free or acylated by (C₁-C₅)-alkoxycarbonyl, (C₆-C₁₂)-arloxycarbonyl, (C₇-C₁₃)-aralkyloxycarbonyl, (C₁-C₆)-alkanoyl, (C₇-C₁₃)-aroyl, arginyl, lysyl-aminocaproyl, or arginyl-arginyl;
A denotes the Phe or an L-2-thienylalanine residue;
B denotes Arg or Lys;
C denotes Ile, Phe, Leu, Val or an L-2-thienylalanine residue;
N' denotes Asp, Glu, Gln, Asn, Leu, Ile, Trp, Asp(OBuᵗ), Glu(OBuᵗ), Glu(OBzl) or a 2-thienylalanine residue, wherein each amino acid is in their L- or D-configuration;
E denotes Gln, Thr, Pro;
F denotes Ser, Thr or Ala, each in their L- or D-configuration;
G denotes Gly, Ala or D-Ala, and
Z represents a residue of the formula II, in which
H denotes Asn, Ser, Pro or Thr, each in their L- or D-form;
I denotes Ser, Thr, Ala or Ser(Buᵗ), each in their L- or D-form;
J denotes Phe or a L-2-thienylalanine residue,
K denotes Arg, Lys, Orn or a bond;
L denotes Tyr or a bond;
M denotes Arg-OH, Arg-NH₂, OH, OR, NH₂, NHR', Gly-Lys-Arg-OH or Gly-Lys-Arg-NH₂;
R denotes unbranched (C₁-C₆)-alkyl, and
R' denotes —[CH₂]ₙNH₂ or —[CH₂]ₙ-NH-C(NH)NH₂, n being an integer and representing 3-8, and its physiologically tolerated salts.

5. A peptide of the formula I as claimed in claim 1, in which
X denotes Ser or Ser-Ser, wherein each Ser is in the L- or D-configuration, and the N-terminal amino group of the amino acid or dipeptide residue being free or being acylated by arginyl-arginyl or ε-aminocaproyl;
A denotes Phe;
B denotes Arg or Lys,
C denotes Ile, Leu, Val or an L-2-thienylalanine residue;
N' denotes Asp, Gln, Leu, Ile, Asp(OBuᵗ), Glu(OBuᵗ), Tyr(Buᵗ) or Tyr(Me);
E denotes Gln, Thr or Pro;
F denotes Ser or Ala, each in their L- or D-configuration;
G denotes Gly, Ala or D-Ala, and
Z represents the residue of the formula II in which
H denotes Asn, Pro or Thr, each in their L- or D-form;
I denotes Ser, Thr or Ala, each in their L- or D-form;
J denotes Phe or a 2-thienylalanine residue;
K denotes Arg, Lys or a bond;
L denotes Tyr, Tyr(Buᵗ) or a bond;
M denotes OH, NH₂, NHR', Gly-Lys-Arg-OH or Gly-Lys-Arg-NH₂, and
R' denotes —[CH₂]₂—NH₂ or —[CH₂]ₙ—NH—C(NH)NH₂, n being an integer and representing 3-8; and its physiologically tolerated salts.

6. A peptide of the formula

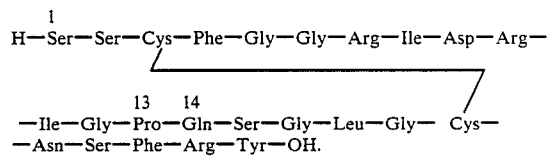

7. A peptide of the formula

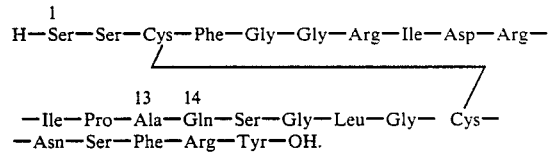

8. A peptide of the formula

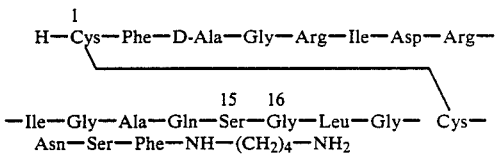

9. A pharmaceutical formulation comprising an amount effective as a pharmaceutical of a compound as claimed in claim 1 and a physiologically tolerated vehicle.

10. A method for diuresis comprising administration of a compound as claimed in claim 1 in an amount having a diuretic effect.

11. A method for vasorelaxation comprising administration of a compound as claimed in claim 1 in an amount having a vasorelaxant effect.

12. A method for reducing the intraocular pressure comprising administration of an effective pressure-reducing amount of a compound as claimed in claim 1.

13. A method for producing natriuresis in a mammal comprising administering to said mammal a compound of the formula I according to claim 1 in an amount having a natriuretic effect.

* * * * *